(12) United States Patent
Geibel et al.

(10) Patent No.: US 9,034,391 B2
(45) Date of Patent: May 19, 2015

(54) COMPOSITIONS WITH ENHANCED BIOAVAILABILITY AND FAST ACTING INHIBITOR OR GASTRIC ACID SECRETION

(75) Inventors: John P. Geibel, Branford, CT (US); Philipp Kirchhoff, Attendorn (DE)

(73) Assignee: YALE UNIVERSITY, New Haven, CT (US)

( * ) Notice: Subject to any disclaimer, the term of this patent is extended or adjusted under 35 U.S.C. 154(b) by 407 days.

(21) Appl. No.: 12/452,637

(22) PCT Filed: Jul. 22, 2008

(86) PCT No.: PCT/US2008/008878
§ 371 (c)(1),
(2), (4) Date: Feb. 12, 2010

(87) PCT Pub. No.: WO2009/017624
PCT Pub. Date: Feb. 5, 2009

(65) Prior Publication Data
US 2010/0150861 A1    Jun. 17, 2010

Related U.S. Application Data

(63) Continuation of application No. 11/881,176, filed on Jul. 26, 2007, now Pat. No. 8,512,761, which is a continuation-in-part of application No. PCT/US2007/001950, filed on Jan. 25, 2007.

(60) Provisional application No. 60/762,595, filed on Jan. 27, 2006, provisional application No. 60/764,834, filed on Feb. 3, 2006, provisional application No. 60/850,891, filed on Oct. 11, 2006.

(51) Int. Cl.
| | | |
|---|---|---|
| *A61K 33/40* | (2006.01) | |
| *A61K 33/30* | (2006.01) | |
| *A61K 31/315* | (2006.01) | |
| *A61K 45/06* | (2006.01) | |

(52) U.S. Cl.
CPC ............. *A61K 33/30* (2013.01); *A61K 31/315* (2013.01); *A61K 45/06* (2013.01)

(58) Field of Classification Search
USPC .................................................. 424/13.2, 614
See application file for complete search history.

(56) References Cited

U.S. PATENT DOCUMENTS

| | | | |
|---|---|---|---|
| 4,292,324 A | | 9/1981 | Jonsson et al. |
| 5,397,784 A | * | 3/1995 | Gazdag et al. ................ 514/283 |
| 6,166,071 A | | 12/2000 | Ashmead et al. |
| 6,596,708 B1 | * | 7/2003 | Petrus ............................ 514/62 |
| 6,613,354 B2 | | 9/2003 | Depui et al. |
| 6,930,099 B2 | | 8/2005 | Petrus |
| 8,512,761 B2 | | 8/2013 | Geibel et al. |
| 2002/0198165 A1 | | 12/2002 | Bratzler et al. |
| 2003/0068326 A1 | | 4/2003 | Gevas et al. |
| 2003/0077333 A1 | | 4/2003 | Phillips et al. |
| 2004/0019102 A1 | * | 1/2004 | Kennedy ....................... 514/476 |

(Continued)

FOREIGN PATENT DOCUMENTS

| | | |
|---|---|---|
| EP | 0303380 A2 | 2/1989 |
| EP | 0942720 B1 | 8/2003 |
| WO | WO 9525513 | 9/1995 |
| WO | WO 9525513 A1 | 9/1995 |
| WO | 9810773 A1 | 3/1998 |
| WO | WO 9816218 | 4/1998 |
| WO | WO-01/72300 A1 * | 10/2001 |
| WO | WO 2003066001 A2 | 8/2003 |
| WO | WO 2004/099182 | 11/2004 |
| WO | WO 2004099182 A1 | 11/2004 |

(Continued)

OTHER PUBLICATIONS

Peulen O, Denis G, Defresne MP and Dandrifosse G. Spermine-Induced alteration of small intestine in suckling rat: involvement of apoptosis or Zn2+ enzymes? Dig Dis Sci 46: 2490-2498, 2001.

(Continued)

*Primary Examiner* — Ali Soroush
(74) *Attorney, Agent, or Firm* — Henry D. Coleman; R. Neil Sudol

(57) ABSTRACT

The present invention relates to the use of pharmaceutically acceptable zinc salts, preferably water soluble zinc salts alone or optionally, in combination with one or more of a protein pump inhibitor (PPI), H2 blocker, anti-*H. pylori* antibiotic/antimicrobial, cytoprotective agent or a combination agent as otherwise described herein for providing fast action with optional long duration effect in reducing gastric acid secretion, raising the pH of the stomach during resting phase as well as decreasing the duration of stomach acid release during a secretagogue phase and for treating conditions including gastroesophageal reflux disease (GERD), non-erosive reflux disease (NERD), Zollinger-Ellison syndrome (ZE disease), ulcer disease, and gastric cancer, as well as preventing or reducing the likelihood of ulcer disease. In addition, the present methods are useful for treating patients who are non-responsive to proton pump inhibitors (PPI) and as an alternative to traditional therapies or conditions which are caused by rapid and complete inhibition of secretagogue induced acid secretion. The present invention also relates to the use of one or more water soluble zinc salts, administered in combination with a therapeutic compound or agent (second therapeutic agent) which may be delivered orally with enhanced bioavailability (compared to compounds which are administered in the absence of water soluble zinc salts) or other favorable benefits. In addition, therapeutic agents which exhibit sensitivity to low pH may be advantageously orally administered in combination with an effective amount of at least one water soluble zinc salt. Compositions according to the present invention exhibit greater bioavailability of the active agent when formulated in combination with a water soluble zinc salt in oral dosage form than when administered with the water soluble zinc salt.

20 Claims, 10 Drawing Sheets

(56) References Cited

U.S. PATENT DOCUMENTS

| | | | |
|---|---|---|---|
| 2004/0058014 A1* | 3/2004 | Steegers-Theunissen et al. | 424/643 |
| 2004/0126333 A1* | 7/2004 | Galli et al. | 424/49 |
| 2004/0180850 A1 | 9/2004 | Natunen et al. | |
| 2004/0248942 A1 | 12/2004 | Hepburn et al. | |
| 2005/0147675 A1 | 7/2005 | Petrus | |
| 2005/0238731 A1 | 10/2005 | Holt | |
| 2006/0235053 A1 | 10/2006 | Gebauer et al. | |
| 2006/0251722 A1 | 11/2006 | Bandak et al. | |
| 2008/0038370 A1 | 2/2008 | Holt | |
| 2009/0035393 A1 | 2/2009 | Geibel et al. | |

FOREIGN PATENT DOCUMENTS

| | | |
|---|---|---|
| WO | WO 2005/011692 | 2/2005 |
| WO | WO 2005011692 A1 | 2/2005 |
| WO | WO 2005/076987 | 8/2005 |
| WO | WO 2005076987 A2 | 8/2005 |
| WO | WO 2006073779 | 7/2006 |
| WO | WO 2007/089511 | 8/2007 |
| WO | WO 2007089511 A2 | 8/2007 |
| WO | WO 2007089511 A2 | 9/2007 |

OTHER PUBLICATIONS

Prinz C, Kajimura M, Scott D, Helander H, Shin J, Besancon M, Bamberg K, Hersey S, Sachs G. Acid secretion and the H,K ATPase of stomach. Yale J Biol Med 1992;65:577-596.
Raugstad TS, Svanes K, Ulven A, Moister A. Interaction between acute gastric ulcer and epinephrine-induced mucosal erosions in the rat: the significance of gastric acid secretion. Digestion 1979;19:70-72.
Robinson M. Drugs, bugs, and esophageal pH profiles. Yale J Biol Med 1999;72:169-172.
Sachs G, Scott D, Reuben M. Omeprazole and the gastric mucosa. Digestion 1990;47 Suppl 1:35-38.
Sachs G, Shin JM, Pratha V, Hogan D. Synthesis or rupture: duration of acid inhibition by proton pump inhibitors. Drugs Today (Barc) 2003;39 Suppi A:11-14.
Sachs G. Physiology of the parietal cell and therapeutic implications. Pharmacotherapy 2003;23:68S-73S.
Sachs G, Walimark B. The gastric H+,K+-ATPase: the site of action of omeprazole. 10 Scand J Gastroenterol Suppl 1989;166:3-11.
Sachs G. The parietal cell as a therapeutic target. Scand J Gastroenterol Suppl 1986;118:1-10.
Sachs G, Prinz C, Loo D, Bamberg K, Besancon M, Shin JM. Gastric acid secretion: activation and inhibition. Yale J Biol Med 1994;67:81-95.
Sanders SW, Moore JG, Day GM, Tolman KG. Circadian differences in pharmacological blockade of meal-stimulated gastric acid secretion. Aliment Pharmacol Ther 1992;6:187-193.
Schultheis PJ, Clarke LL, Meneton P, Harlin M, Boivin GP, Stemmermann G, Duffy JJ, Doetschman T, Miller ML, Shull GE. Targeted disruption of the murine Na+/H+ exchanger isoform 2 gene causes reduced viability of gastric parietal cells and loss of net acid secretion. J Clin Invest 1998;101:1243-1253.
Scott DR, Helander HF, Hersey SJ, Sachs G. The site of acid secretion in the mammalian parietal cell. Biochim Biophys Acta 1993;1146:73-80.
Shamburek RD, Schubert ML. Pharmacology of gastric acid inhibition. Baillieres Clin Gastroenterol 1993;7:23-54.
Singh J. Prostaglandin release from rat stomach following vagal stimulation or administration of acetylcholine. Eur J Pharmacol 1980;65:39-48.
Soumarmon A, Lewin MJ. Gastric (H+,K+)-ATPase. Biochimie 1986;68:1287-1291.
Sunderman Fw, Jr. The influence of zinc on apoptosis. Ann Clin Lab Sci 1995;25:134-142.
Tutuian R, Katz PO, Castell DO. Nocturnal acid breakthrough: pH, drugs and bugs. Eur J Gastroenterol Hepatol 2004;16:441-443.
Tytgat GN. Shortcomings of the first-generation proton pump inhibitors. Eur J Gastroenterol Hepatol 2001;13 Suppl 1: S29-S33.
Urushidani T, Forte JG. Signal transduction and activation of acid secretion in the parietal cell. J Membr Biol 1997;159:99-111.
Waisbren SJ, Geibel J, Boron WF, Modlin IM. Luminal perfusion of isolated gastric glands. Am J Physiol 1994;266:01013-C1027.
Waisbren SJ, Geibel JP, Modlin IM, Boron WF. Unusual permeability properties of gastric gland cells. Nature 1994;368:332-335.
Waisbren SJ, Modlin IM. The evolution of therapeutic vagotomy. Surg Gynecol Obstet 1990;170:261-272.
Wallmark B, Lorentzon P, Sachs G. The gastric H+,K(+)-ATPase. J Intern Med Suppl 1990;732:3-8.
Watanabe T, Arakawa T, Fukuda T, Higuchi K, Kobayashi K. Zinc deficiency delays gastric ulcer healing in rats. Dig Dis Sci 1995;40:1340-1344.
Williams JL. Gastroesophageal reflux disease: clinical manifestations. Gastroenterol Nurs 2003;26:195-200.
Wolfe MM, Welage LS, Sachs G. Proton pump inhibitors and gastric acid secretion. Am J Gastroenterol 2001;96:3467-3468.
Benson DA, Karsch-Mizrachi I, Lipman DJ, Ostell J, Rapp BA, Wheeler DL Nucl. Acids Res. 28:15-18 (2000).
Cho CH Ogle CW and Dai S, Effects of Zinc Sulphate Pretreatment on Gastric Acid Secretion and Lesion Formation in Rats infused Intravenously with Graded Doses of Methacholine. Pharmacology 17:32-38 (1978).
Green OP, Deoraj P, Gopoinath C, Crook D, Matsuda K. Toxxicity of the novel antipeptic ulcer agent catena-(S)-[mu-(3-aminopropionyl)histidinato (2-)-N1,N2, Q:N tau]-zinc in male cynomolgus monkets. Arzneimittelforschung. May 1993; 43:562-9.
Kuwayama J, Takahashi M, Suzuki K, Suga M, Takata H, Ohara T, Koizumi K, Kiriyama Y. Polaprezinc. Nippon Rinsho. Feb. 2002; 60 Suppl 2:717-20. Review. Japanese . No Abstract Available.
Matsuda K, Yamaguchi I, Wada H.,Toxicity of the novel anti-peptic ulcer agent polaprrezinc in beagle dogs. Arzneimittelforschung. Jan. 1995; 45:52-60.
Otaka M. Chaperon-induction therapy for peptic ulcers. Nippon Rinsho. Feb. 2002; 60 Suppl 2:572-6. Review. Japanese . No abstract available.
Nishiwaki H, Kato S. Takeuchi K. Irritant action of monochloramine in rat stomachs: effects of zinc L-carnosine (polaprezinc)Gen Pharmacol. Nov. 1997; 29 : 713-8.
Varas Lorenzo M J, Lopez Martinez A; Gordillo Bernal J; Mundet Surroca J; Hospital Creu Roja, L'Hospitalet de Llobregat Revista Espanola de enfermedades digestivas: organo official de la Sociedad Espanola de Patologia Digestiva (1991) 80: 91-4 [ISSN 1130-0108].
Yoshikawa T, Naito Y, Tanigawa T, Yoneta T, Kondo M. The antioxidant properties of a novel zinc-carnosine chelate compound, N-(3-aminopropionyl)-L-histidinato zinc. Biochim Biophys Acta Nov. 14, 1991; 1115:15-22.
Functional Ingredients Staff, Zinc Carnosine a New Peptic Ulcer Treatment. Functional Ingredients Nov. 2002, 2pp.
Nascimento, JW, et al., Anti-Inflammatory Activity and Gastric Lesions Induced by Zinc-Tenoxicam. Pharmacology 2003; 68:64-69.
Suzuki, K, et al., Prostaglandin E Inhibits Indomethacin-Induced Gastric Lesions through EP-1 Receptors. Digestion 2001; 63:92-101.
Conchillo, A et al., Cytoprotective and antisecretory activity of a ranitidine-zinc complex. Prostaglandins Leukot Essent Fatty Acids. Jun. 1995;52(6):393-7.
Ozutemiz, A O, et al., Effect of omeprazole on plasma zinc levels after oral zinc administration. Indian Journal of Gastroenterology 2002;21:216-218.
Serfaty-Lacrosniere, C., et al., Hypochlorhydria from Short-Term Omeprazole Treatment Does Not Inhibit Intestinal Absorption of Calcium, Phosphorus, Magnesium or Zinc from Food in Humans. Journal of the American College of Nutrition. 1995;14:364-368.
Reed, J C, et al., Apoptosis-based therapies for hematologic malignancies. Blood. 2005;106:408-418.
Rainsford, K D, et al., Anti-ulcer Activity of a Slow-release Zinc Complex, Zinc Monoglycerolate (Glyzinc). J. Pharm. Pharmacol. Jun. 1992;44(6):476-482.
Bandyopadhyay, B , et al., Protective effect of zinc gluconate on chemically induced gastric ulcer. Indian J. Med. Res. Jul. 1997; 106:27-32.

(56) References Cited

OTHER PUBLICATIONS

Cho, C H, et al., Effects of Zinc Chloride on Gastric Secretion and Ulcer Formation in Pylorus-Occluded Rats. European Journal of Pharmacology 1976;38:337-341.
Aarimaa M, Soderstrom KO, Kalimo H, lnberg M, Nevalainen T. Morphology and function of the parietal cells after proximal selective vagotomy in duodenal ulcer 20 patients. Scand J Gastroenterol 1984;19:787-797.
Abelo A, Eriksson UG, Karlsson MO, Larsson H, Gabrielsson J. A turnover model of irreversible inhibition of gastric acid secretion by omeprazole in the dog. J Pharmacol Exp Ther 2000;295:662-669.
Adachi K, Komazawa Y, Fujishiro H, Mihara T, Ono M, Yuki M, Kawamura A, Karim Rumi MA, Amano Y, Kinoshita Y. Nocturnal gastric acid breakthrough during the administration of rabeprazole and ranitidine in Helicobacter pylori-negative subjects: effects of different regimens. J Gastroenterol 2003;38:830-835.
Aihara T, Nakamura E, Arnagase K, Tomita K, Fujishita T, Furutani K, Okabe S. Pharmacological control of gastric acid secretion for the treatment of acid-related peptic disease: past, present, and future. Pharmacol Ther 2003;98:109-127.
Alino SF, Garcia D, Uvnas-Moberg K. On the interaction between intragastric pH and electrical vagal stimulation in causing gastric acid secretion and intraluminal release of gastrin and somatostatin in anesthetized rats. Acta Physiol Scand 1983;117:491-495.
Amdrup E. The surgical treatment of duodenal ulcer. Schweiz Med Wochenschr 1979;109:583-585.
Andersen JB, Andrade DV, Wang T. Effects of inhibition gastric acid secretion on arterial acid-base status during digestion in the toad Bufo marinus. Comp Biochem Physiol a Mol lntegr Physiol 2003;135:425-433.
Andersson K, Carlsson E. Potassium-competitive acid blockade: a new therapeutic strategy in acid-related diseases. Pharmacol Ther 2005;108:294-307.
Babenko GA and Parashchak AP. [Iron, copper, cobalt and zinc contents of gastric juice of dogs with experimental stomach ulcer]. Patol Fiziol Eksp Ter 12: 65-67, 1968.
Bell NJ, Hunt RH. Progress with proton pump inhibition. Yale J Biol Med 1992;65:649-657.
Blachar A, Federle MP. Gastrointestinal complications of laparoscopic roux-en-Y gastric bypass surgery in patients who are morbidly obese: findings on radiography and CT. AJR Am J Roentgenol 2002;179:1437-1442.
Brzozowski T, Konturek PC, Konturek SJ, Drozdowicz D, Kwiecien S, Pajdo R, Bielanski W, Hahn EG. Role of gastric acid secretion in progression of acute gastric erosions induced by ischemia-reperfusion into gastric ulcers. Eur J Pharmacol 2000;398:147-158.
Busque SM, Kerstetter JE, Geibel JP, Insogna K. L-type amino acids stimulate gastric acid secretion by activation of the calcium-sensing receptor in parietal cells. Am J Physiol Gastrointest Liver Physiol 2005;289:G664-G669.
Carlsson R, Galmiche JP, Dent J, Lundell L, Frison L. Prognostic factors influencing relapse of oesophagitis during maintenance therapy with antisecretory drugs: a meta-analysis of long-term omeprazole trials. Aliment Pharmacol Ther 1997;11:473-482.
Cho CH, Fong LY, Ma PC, Ogle CW. Zinc deficiency: its role in gastric secretion and stress-induced gastric ulceration in rats. Pharmacol Biochem Behav 1987;26:293-297.
Cho CH, Fong LY, Wong SH, Ogle CW. Zinc deficiency worsens ethanol-induced gastric ulcers in rats. Drug Nutr Interact 1988;5:289-295.
Dammann HG, Burkhardt F. Pantoprazole versus omeprazole: influence on meal stimulated gastric acid secretion. Eur J Gastroenterol Hepatol 1999;11:1277-1282.
Diamond I, Hurley LS. Histopathology of zinc-deficient fetal rats. J Nutr 1970;100:325-329.
Dufner MM, Kirchhoff P, Remy C, Hafiier P, Muller MK, Cheng SX, Tang LQ, Hebert SC, Geibel JP, Wagner CA. The calcium-sensing receptor acts as a modulator of gastric acid secretion in freshly isolated human gastric glands. Am J Physiol Gastrointest Liver Physiol 2005;289:G1084-G1090.

Elmes ME, Jones JG. Ultrastructural studies on Paneth cell apoptosis in zinc deficient rats. Cell Tissue Res 1980;208:57-63.
Fong LY, Lee JS, Chan WC, Newberne PM. Zinc deficiency and the development of esophageal and forestomach tumors in Sprague-Dawley rats fed precursors of N-nitroso-N-benzyl.methylamine. J Natl Cancer Inst 1984;72:419-425.
Forte JG, LY B, Rong Q, Ogihara S, Ramilo M, Agnew B, Yao X. State of actin in gastric parietal cells. Am J Physiol 1998;274:C97-104.
Franzin G, Manfrini C, Musola R, Rodella S, Fratton A. Chronic erosion of the stomach—a clinical, endoscopic and histological evaluation. Endoscopy 1984;16:1-5.
Frommer DJ. The healing of gastric ulcers by zinc sulphate. Med J Aust 1975;2:793-796.
Gardner JD, Sloan S, Miner PB, Robinson M. Meal-stimulated gastric acid secretion and integrated gastric acidity in gastro-oesophageal reflux disease. Aliment Pharmacol Ther 2003;17:945-953.
Garnett WR. Lansoprazole: a proton pump inhibitor. Ann Pharmacother 1996;30:1425-1436.
Gedda K, Scott D, Besancon M, Lorentzon P, Sachs G. Turnover of the gastric H+,K(+)-adenosine triphosphatase alpha subunit and its effect on inhibition of rat gastric acid secretion. Gastroenterology 1995;109:1134-1141.
Geibel JP, Wagner CA, Caroppo R, Qureshi I, Gloeckner J, Manuelidis L, Kirchhoff P, Radebold K. The stomach divalent ion-sensing receptor scar is a modulator of gastric acid secretion. J Biol Chem 2001,276:39549-39552.
Geibel JP. Secretion and absorption by colonic crypts. Annu Rev Physiol 2005;67:471-490.
Geibel R. Role of potassium in acid secretion. World J Gastroenterol 2005;11:5259 5265.
Helander HF, Keeling DJ. Cell biology of gastric acid secretion. Baillieres Clin Gastroenterol 1993,7:1-21.
Hersey SJ, Sachs G. Gastric-Acid Secretion. Physiological Reviews 1995;75:155-189.
Hirschowitz BI, Keeling D, Lewin M, Okabe S, Parsons M, Sewing K, Wallmark B, Sachs G. Pharmacological Aspects of Acid-Secretion. Digestive Diseases and Sciences 1995;40:S3-S23.
Horie S, Yano S, Watanabe K. Effects of drugs acting on Cl(-)-. Eur JPharmacol 1992;229:15-19.
Houghton J, Stoicov C, Nomura S, Rogers AB, Carlson J, Li H, Cai X, Fox JG, Goldenring JR, Wang TC. Gastric cancer originating from bone marrow-derived cells. Science 2004;306:1568-1571.
Katz PO, Hatlebakk JG, Castell DO. Gastric acidity and acid breakthrough with twice-daily omeprazole or lansoprazole. Aliment Pharmacol Ther 2000;14:709-714.
Kirchhoff P, Wagner CA, Gaetzschmann F, Radebold K, Geibel R. Demonstration of a functional apical sodium hydrogen exchanger in isolated rat gastric glands. Am J Physiol Gastrointest Liver Physiol 2003;285:G1242-G1248.
Kirchhoff P, Andersson K, Socrates T, Sidani SM, Kosiek 0, Geibel JP. Characteristics of the K+-competitive H-F,K+-ATPase Inhibitor AZD0865 in isolated rat gastric glands. Am J Physiol Gastrointest Liver Physiol 2006.
Kirchhoff P, Dave MH, Remy C, Kosiek 0, Busque SM, Dufner M, Geibel JP, Verrey F, Wagner CA. An amino acid traliporter involved in gastric acid secretion. Pflugers Arch 2006,451:738-748.
Kleinman L, McIntosh E, Ryan M, Schmier J, Crawley J, Locke GR, III, De LG. Willingness to pay for complete symptom relief of gastroesophageal reflux disease.Arch Intern Med 2002;162.1361-1366.
Knauf F, Yang CL, Thomson RB, Menton SA, Giebisch G, Aronson PS. Identification of a chloride-formate exchanger expressed on the brush border membrane of renal proximal tubule cells. Proc Natl Acad Sci U S A 2001;98:9425-9430.
Lehmann F, Hildebrand P, Beglinger C. New molecular targets for treatment of peptic ulcer disease. Drugs 2003;63:1785-1797.
Locke GR, M. Current medical management of gastroesophageal reflux disease. Thorac Surg Clin 2005;15:369-375.
Lorentzon P, Scott D, Hersey S, Wallmark B, Rabon E, Sachs G. The gastric H+,K+-ATPase. Frog Clin Biol Res 1988;273:247-254.

(56) References Cited

OTHER PUBLICATIONS

McDaniel N, Lytle C. Parietal cells express high levels of Na—K—2Cl cotransporter on migrating into the gastric gland neck. Am J Physiol 1999;276:G1273-G1278.

Meulemans AL, Eelen JG, Schuurkes JA. No mediates gastric relaxation after brief vagal stimulation in anesthetized dogs. Am J Physiol 1995;269:G255-G261.

Naess K. [Zinc in the treatment of stomach ulcer]. Tidsskr nor Laegeforen 1976;96:1334.

Ng WL, Fong LY, Ma L, Newberne PM. Dietary zinc deficiency and tumorigenesis: a scanning electron microscope study. J Electron Microsc (Tokyo) 1984;33:344-348.

Peghini PL, Katz PO, Bracy NA, Castell DO. Nocturnal recovery of gastric acid secretion with twice-daily dosing of proton pump inhibitors. Am J Gastroenterol 1998;93:763-767.

Peghini PL, Katz PO, Castell DO. Ranitidine controls nocturnal gastric acid breakthrough on omeprazole: a controlled study in normal subjects. Gastroenterology 1998;115:1335-1339.

Cho C.H. et al., Effects of Zinc Sulphate Pretreatment on Gastric Acid Secretion and Lesion Formation in Rats Infused Intravenously with Graded Doses of Methacholine Pharmacology. 1978, 17(1), 32-38.

Cho C H, et al.; Effects of Zinc Chloride on Gastric Secretion and Ulcer Formation in Pylorus-Occluded Rats; European Journal of Pharmacology 1976; 38:337-341.

Kuwayama H et al.; study of peptic ulcer in the time of H. pylori. Nippon Rinsho (Japanese Clinics) (extra edition) 2002; 60 (Suppl. 2): 717-720.

Clinical Research on Zinc Acexamate for the Treatment of Helicobacter Pylori-related Gastric Ulcers. Anthology of Medicine 2000 (Dec.), 19(6), 870-871. (Chinese language article and its English language translation).

Wang Shenghao, Zhang Xinyue, Zheng Gaoli, Lin Fang, Chen Jue. Study on the Action of Norfloxacin Zinc Against Experimental Gastric Ulcer in Rats; China Pharmacy 2001 (Nov.), 12(11), 650-652. (Chinese language article and its English language translation).

Puscas I et al.; Effect of ZnSO4 upon gastric acid secretion and carbonic anhydrase. International Journal of Clinical Pharmacology, Therapy and Toxicology Jan. 1, 1985; Vol. 23, pp. 609-612. ISSN: 0174-4879.

Cho, C. H. et al., the effects of Zinc Sulphate on Vagal-Induced Mast Cell Changes and Ulcers in the Rat Stomach; European Journal of Pharmacology 1977; 43:315-322.

McLeay, I.. M. et al.; Effects of intraruminal administration of zinc on gastric acid secretion in sheep; Research in Veterinary Science 1977; 23:243-245.

Yamaguchi et al.; Effect of Zinc on the Acidity of Gastric Secretion in Rats. Jul. 1980, Toxicology and Applied Pharmacology, 54:526-530.

Arakawa et al.; Effects of Zinc L-Carnosine on Gastric Mucosal and Cell Damage Caused by Ethanol in Rats. May 1990; Digestive Diseases and Sciences 35(5):559-566.

Gardner JD et al; Measurement of meal-stimulated gastric acid secretion by in vivo gastric autotitration. 2002; J. Appl. Physiol. 92:427-434.

Ghosh T et al.; Review article: methods of measuring gastric acid secretion; 2011; Alimentary Pharmacology and Therapeutics 33:768-781.

Kirchhoff P et al.; Zinc Salts Provide a Novel, prolonged and Rapid Inhibition of Gastric Acid Secretion; 2011; Am J Gasroenterol 106:62-70.

Robinson M et al.; proton Pump Inhibitor Attitudes and Usage: A Patient Survey; Apr. 2002; P & T 27(4): 202-206.

Testerman TL et al..; Nutritional Requirements and Antibiotic Resistance Patterns of Helicobacter Species in Chemically Defined Media; May 2006; Journal of Clinical Microbiology 44(5): 1650-1658.

Jeejeebhoy, K. N. ; Short bowel syndrome: a nutritional and medical approach. Canadian Medical Association Journal May 14, 2002; 166:1297-1302.

\* cited by examiner

Figures 1A-E

Figures 7A-C
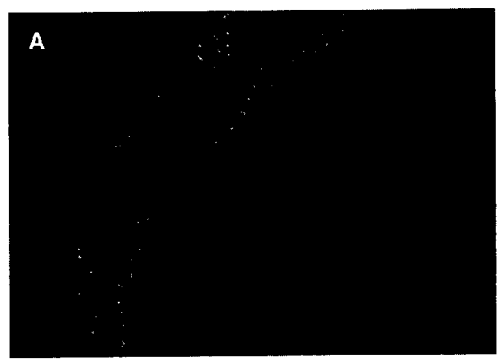

Figures 8A-D
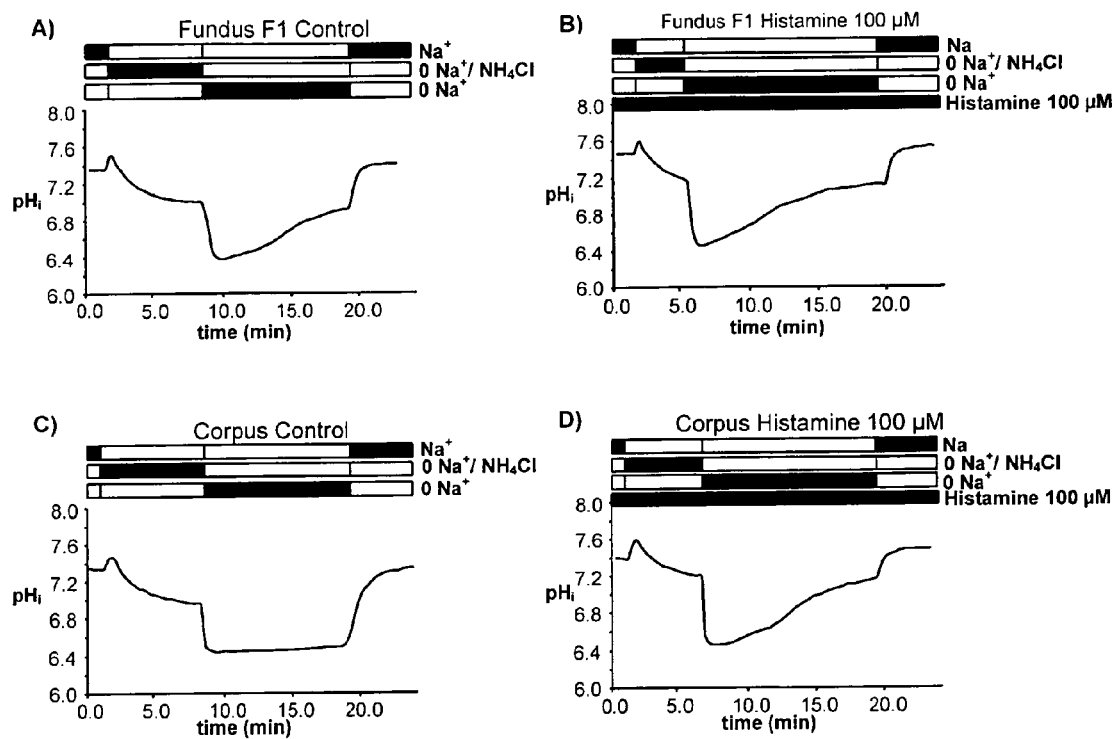

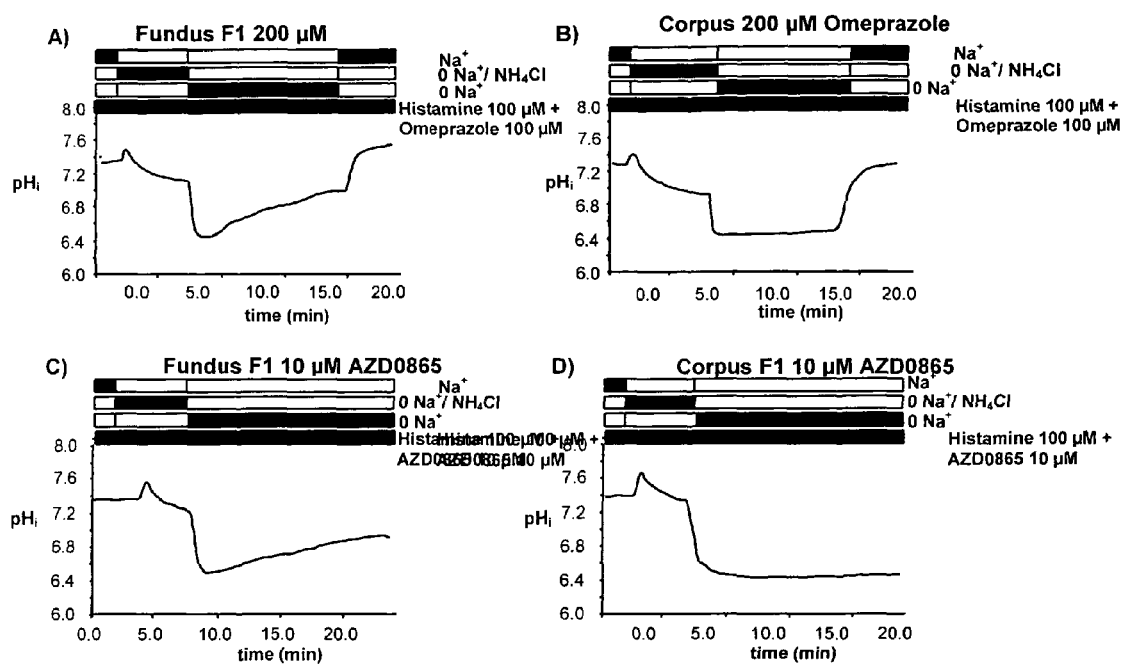
Figures 10A-D

COMPOSITIONS WITH ENHANCED BIOAVAILABILITY AND FAST ACTING INHIBITOR OR GASTRIC ACID SECRETION

RELATED APPLICATIONS

This application claims the benefit of priority of U.S. patent application Ser. No. 11/881,176, filed Jul. 26, 2007, entitled "Fast Acting Inhibitor of Gastric Acid Secretion", which is a continuation-in-part of International patent application serial number PCT/US07/01950, filed Jan. 25, 2007, (which entered the United States National stage as U.S. Ser. No. 12/086,379, filed Sep. 24, 2008.) which claims benefit of U.S. provisional patent application Ser. No. 60/762,595, filed Jan. 27, 2006; U.S. 60/764,834, filed Feb. 3, 2006 and U.S. 60/850,891, filed Oct. 11, 2006. All of said applications are herein incorporated by reference in their entirety.

GOVERNMENT SUPPORT

This invention was made with government support under grant no. DK050230 awarded by the National Institutes of Health. The government has certain rights in the invention.

FIELD OF THE INVENTION

The present invention relates to the use of pharmaceutically acceptable zinc salts, preferably water soluble zinc salts alone or optionally, in combination with one or more of a protein pump inhibitor (PPI), H2 blocker, anti-*H. pylori* antibiotic/antimicrobial, cytoprotective agent or a combination agent as otherwise described herein for providing fast action with optional long duration effect in reducing gastric acid secretion, including acid secretion in the fundus (by inhibiting vacuolar $H^+$-ATPase or $H^+/K^+$-ATPase) and upper body region of the stomach (by inhibiting $H^+/K^+$-ATPase), thus raising the pH of the stomach during resting phase as well as decreasing the duration of stomach acid release during a secretagogue phase and for treating conditions including gastroesophogeal reflux disease (GERD), non-erosive reflux disease (NERD), Zollinger-Ellison syndrome (ZE disease), ulcer disease, and gastric cancer, as well as preventing or reducing the likelihood of ulcer disease. In addition, the present methods are useful for treating patients who are nonresponsive to proton pump inhibitors (PPI) and as an alternative to traditional therapies or conditions which are caused by rapid and complete inhibition of secretagogue induced acid secretion.

The present invention also relates to the use of one or more water soluble zinc salts, administered in combination with a therapeutic compound or agent (second therapeutic agent) which may be delivered orally with enhanced bioavailability (compared to compounds which are administered in the absence of water soluble zinc salts) or other favorable benefits. In addition, therapeutic agents which exhibit sensitivity to low pH may be advantageously orally administered in combination with an effective amount of at least one water soluble zinc salt. Compositions according to the present invention exhibit greater bioavailability of the active agent when formulated in combination with a water soluble zinc salt in oral dosage form than when administered with the water soluble zinc salt.

BACKGROUND OF THE INVENTION

The generation of concentrated 0.16N hydrochloric acid by the mammalian parietal cell involves a complex combination of neuronal and hormonal regulatory feedback loops[1-3]. Following activation of the cell there is a complex cellular transfer of ions that allows for the formation of acid[4-7]. A disruption in any of these components (secretory receptors, or ion transporters) can lead to either a cessation in the secretion of acid, or in the hypersecretion of acid. In the latter over 30 million patients per year suffer from symptoms of acid related diseases with the numbers increasing yearly[8-11]. Clinically the uncontrolled release or the continued hypersecretion of acid can lead to changes in both gastric and intestinal epithelium, but can in more serious cases lead to erosions of the esophagus that can result in metaplasia and death[12-14]. Recent evidence has also emerged that prolonged recurrent periods of hypersecretory states can lead to gastric carcinoid formation[15].

In an attempt to design therapies to prevent hyperacid secretion a variety of approaches have been employed in recent years with two of the most successful being: a) inhibition of the Histamine receptor on the basolateral membrane of the parietal cell, b) proton pump specific drugs targeted against the $H^+,K^+$-ATPase (the so called proton pump inhibitors; PPI)[16]-18. Both of these therapies have greatly improved the quality of life for patients suffering from this disease, however there is an ever increasing number of patients that have experienced recurrent disease while still taking the drugs[19, 20]. Despite their high degree of efficacy and worldwide clinical use, failure in the treatment of acid related diseases has been reported and the degree and speed of onset of symptom relief are important to patients[21]. It has been estimated that about 30% of GERD patients remain symptomatic on standard dose of PPI[22]. Furthermore PPI's have a short plasma half life which often leads to nocturnal acid breakthrough[23]. Therapeutic oral doses of PPIs reach steady state and thus achieve their maximal effective levels after 4-5 days with typical dosing regimens[24]. This slow and cumulative onset of effect of PPIs relates to their ability to inhibit only those pumps which are active when the PPI drug is available. After PPI administration, there is a return of acid secretion that is partly due to de novo synthesis of the enzyme[25].

Zinc is an essential part of the diet that all cells require in order to maintain membrane integrity and function. Deficiency in intracellular zinc leads to apoptotic events, and cell death[26-30]. Previous studies have investigated the potential role of zinc in the proliferation and generation of the protective barrier, namely the mucous gel layer at the surface of the stomach[31-34]. These studies falsely attributed the reduction in acid secretion to an increase in the thickness of the gel layer.[33-35].

Gastric acid aids protein digestion; facilitates the absorption of iron, calcium, and vitamin B12; and prevents bacterial overgrowth. When levels of acid and proteolytic enzymes overwhelm the mucosal defense mechanisms, ulcers occur. To avoid damage that is associated with these harsh conditions, gastric acid must be finely regulated by overlapping neural (e.g. acetylcholine), hormonal (e.g. gastrin and ghrelin), and paracrine (e.g. histamine and somatostatin) pathways, and more recently via the Calcium Sensing Receptor. Any long term alterations in any of these regulatory pathways leads to cell and tissue destruction and clinical manifestations such as peptic ulcer diseases, or gastroesophageal reflux disease (GERD). Two methods are commonly employed to treat the overproduction of acid: a) surgically, by elimination of the neuronal element (vagotomy) or b) pharmacologically, either through histamine 2 receptor antagonists or proton pump inhibitors (PPI's) or a combination of both.

PPI's such as omeprazole are irreversible inhibitors of the gastric $H^+,K^+$-ATPase, recently various derivatives of the parent compound omeprazole that bind to multiple cysteine residues on the exofacial surface of the $H^+,K^+$-ATPase have been developed in hopes of having a tighter molecular binding, and longer action have been employed. Both rabeprazole, and lansoprazole are examples of these multiple binding drugs and are activated in the acidic lumen of the gastric gland and modify the cysteine residues located on the luminal surface of the $H^+,K^+$-ATPase. In the resting cell the acid secreting pumps are internalized in a system of tubular vesicles, and are in such a conformational state that the PPIs can only inhibit the $H^+,K^+$-ATPases which have already been activated and transferred to the apical surface of the parietal cell.

Although optimizing pharmacological profiles within the PPI class may provide some clinical benefit, other areas of research may prove to be more fruitful and furthermore the fine tuning of the acid secretory process is still not completely understood and remains an important target for therapies to modulate gastric acid secretion.

Zinc is required for a large number of biological processes including gene expression, replication, membrane stability, hormonal storage and release and as a catalytic component for enzymes. There has been no investigation of the actions of zinc at the cellular level relating to effects on acid secretion.

*Helicobacter pylorus* resides within the mucous layer of the human gastric mucosa. Due to extremely low pH, the stomach is a hostile environment to most other microorganisms. The ability of *H. pylori* to flourish in the stomach has been attributed to protective mechanisms such as its production of urease, protecting the bacterium from gastric acidity by creating a basic microenvironment, See, Taylor and Blaser, *Epidemiol Rev,* 13:42-59, (1991).

The stomach is a large organ that can be divided into 3 main zones that are involved in the process of digestion of foodstuff and the sterilization of liquids and water. When defining the functional process of the stomach it has been commonly divided into two zones: Upper Stomach, and Lower Stomach. The upper stomach, is thought to be composed of the fundus and upper body, and shows low frequency, sustained contractions that are responsible for generating a basal pressure within the stomach. Of note is that these tonic contractions also generate a pressure gradient from the stomach to small intestine and are responsible for gastric emptying. Interestingly, when swallowing food and the consequent gastric distention that occurs acts to inhibits contraction of this region of the stomach, allowing it to balloon out forming a large reservoir without a significant increase in pressure. The lower stomach is thought to be involved in the grinding and liquefaction of the foodstuffs by the secretion of HCl from the parietal cells found in this section of the stomach.

BRIEF DESCRIPTION OF THE FIGURES

FIGS. 7A-C show the immunohistochemistry in rat stomach fundus. (A) Immunolocalization of the gastric $H^+$, $K^+$-ATPase a subunit in rat fundic gland parietal cells (40×). (B) Fundic parietal cell Electron Microscopy of Gold Tagged $H^+$, $K^+$-ATPase protein. Here the nucleus, apical membrane and canaliculus like structure can be seen (8,000×). (C) Higher magnification (25,000×) of the same cell. Here the gold tagged $H^+$, $K^+$-ATPase protein can be seen distributed at the borders of the canaliculus like structure (arrows). (In this figure: n=nucleus, c=canaliculus like structure, am=apical membrane)

FIGS. 8A-D show the original tracing of basal acid secretion and histamine induced acid secretion in the gastric fundus and corpus. Single rat gastric glands were isolated, loaded with pH sensitive dye BCECF to measure intracellular pH of Single parietal cells and the pHi recovery rate was calculated from the slope after an acid load using the $NH_4CL$ prepulse technique. (A) Original tracing of an F1 gland alkalinization (proton efflux) after removing $Na^+$ out of the perfusion bath. (B) Intracellular alkalinization of an F1 gland stimulated by histamine (100 μM) in the absence of extracellular $Na^+$ as a function of $H^+$, $K^+$-ATPase. (C) Tracing of a corpus gland alkalinization under resting condition. (D) Intracellular alkalinization of an corpus gland stimulated by histamine (100 μM) in the absence of extracellular $Na^+$ as a function of $H^+$, $K^+$-ATPase.

FIGS. 10A-D shows original tracing of acid secretion comparing F1 glands and Corpus glands with Omeprazole and AZD0865. Single rat gastric glands were isolated, loaded with the pH sensitive dye BCECF to measure intracellular pH over single parietal cells and the pHi recovery rate was calculated from the slope after an acid load using $NH_4Cl$ prepulse technique as described previously. (A) Original tracing of an intracellular pH measurement demonstrating a F1 gland alkalinization after stimulation by histamine (100 μM). This tracing shows that omeprazole (200 μM) does not inhibit acid secretion in F1 glands. (B) Corpus gland tracing of intracellular alkalinization after stimulation with histamine (100 μM). This tracing shows that Omeprazole (200 μmolar) inhibits acid secretion in the corpus with a intracellular alkalinization rate of (0.014±0.002 $\Delta pH_i$/min. (C) Intracellular tracing of pH measurements demonstrating that AZD0865 does not completely inhibit proton extrusion in the fundus as it does in the corpus. In fundic glands which have been exposed to 10 μM of AZD0865 the intracellular recovery is 0.031±0.006 $\Delta pH_i$/min. (D) In the corpus AZD0865 shows strong inhibition of potassium dependant recovery with intracellular alkalinization rates of 0.021±0.008 $\Delta pH_i$/min.

BRIEF DESCRIPTION OF THE INVENTION

Figure 1:
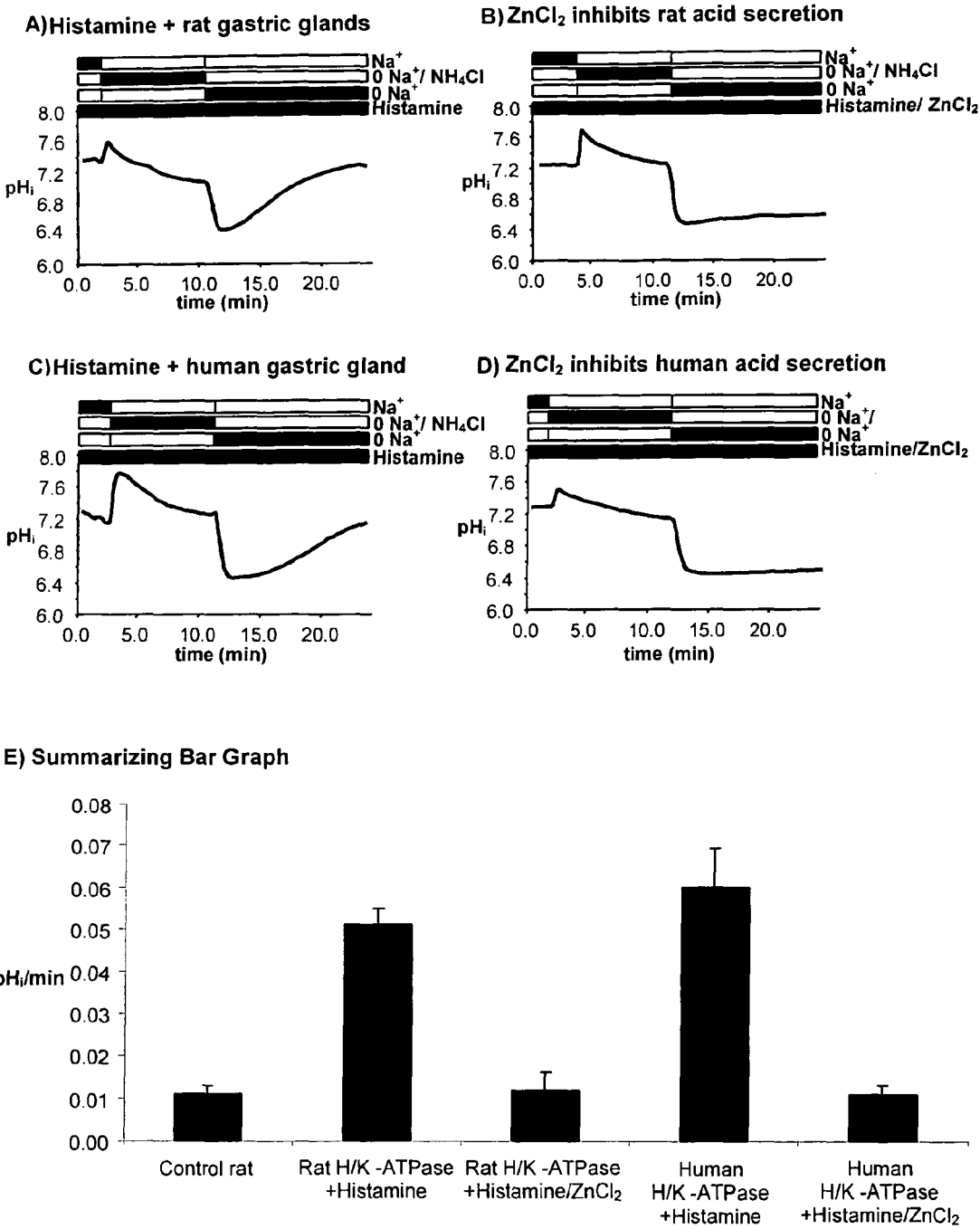
FIGS. 1A-E shows the original tracing of basal acid secretion, histamine induced acid secretion and inhibition by $ZnCl_2$. Single human and rat gastric glands were isolated, loaded with the pH-sensitive dye BCECF to measure intracellular pH over single parietal cells and the pH, recovery rate was calculated from the slope after an acid load using the $NH_4Cl$ prepulse technique. (A,C) Intracellular alkalinization stimulated by histamine (100 μM) in the absence of extracellular $Na^+$ as a function of $H^+/K^+$-ATPase in gastric glands. (B,D) Histamine induced proton efflux from gastric glands can be blocked by 300 umol $ZnCl_2$. (E) Bar graph summarizing data as means SE (control: n=32 cells, 3 gland, 3 animals; histamine: n=120 cells, 15 glands, 8 animals; histamine+ $ZnCl_2$: n=60 cells, 6 gland, 4 animals).

The present invention relates to novel compositions and methods for the rapid inhibition of acid secretion that has little to no potential for side effects. In a first aspect, the present invention relates to zinc compositions comprising at least one pharmaceutically compatible zinc salt (preferably a water soluble salt) in an effective amount which produces a rapid decrease (i.e., within a period of no greater than about 5 minutes, no greater than about 10 minutes, no greater than about 20 minutes, no greater than about 30 minutes, no greater than one hour) of acid secretion in a patient's stomach with a resulting increase (elevation) in stomach pH to an intragastric pH level of at least about 3.0-3.5, at least about 4.0, about 4.0 to about 5.0. In this aspect of the invention, a patient who is in need of an increase of stomach pH is treated with an effective amount of a pharmaceutically compatible zinc salt such that rapid onset of elevated pH within the stomach occurs. This method invention relies on the administration (preferably by, but not limited to, ingestion) of an effective amount of at least one pharmaceutically compatible, preferably water-soluble zinc salt and in which a substantial portion dissolves in the gastric juices at low pH (generally less than about 2.0) and preferably within a range pH from low pH (about 1.0 to about 2.0) to higher pH (about 5.5 to about 7.5 or higher) such that effective amounts of zinc salt may be administered to provide an initial rapid inhibition of acid release and a subsequent maintenance of inhibition of acid release in the stomach. In the present invention, inhibition of gastric acid is inhibited preferably within a rapid period of about 20 minutes to about 1 hour (generally, within a period no greater than about 5 minutes, within a period no greater than about 10 minutes or within a period no greater than about 20 minutes, within a period no greater than about 30 minutes, within a period no greater than about one hour).

The rapid decrease of acid secretion in the patient's stomach occurs throughout the stomach (in both the upper stomach and lower stomach through inhibition of $H^+,K^+$-ATPase), although localized effects of compounds according to the present invention in the upper stomach, especially in the fundic region of the stomach (through inhibition of a second distinguishable protein $H^+$-ATPase) and/or the upper body of the upper stomach (through inhibition of $H^+,K^+$-ATPase). Thus, an additional aspect of the invention is directed to the use of effective amounts of pharmaceutically acceptable zinc compounds for the inhibition of $H^+,K^+$-ATPase (generally throughout the stomach, H+-ATPase (primarily in the fundic region of the stomach) and preferably both. The finding that the present compounds may be used to inhibit $H^+$-ATPase in the fundic region has important clinical ramifications for the following reasons:

1) The erosion of the esophagus by exposure to acid has life threatening consequences due to either internal bleeding, ulceration, and or gastric carcinoid formation by the prolonged exposure to acid. Pursuant to the present invention, as is now demonstrated—glands in the fundus are in direct proximity to the esophageal juncture, that they will secrete acid and can be inhibited by compounds according to the present invention, thus making the present compounds particularly effective in treating GERD, NERD and related conditions.

2) There is an ever increasing number of patients that are becoming insensitive to PPI (proton pump inhibitors) and have recurrent symptoms of acid reflux disease. The protein that we identified in the fundic glands is not sensitive to PPI's and could be the reason that these patients do not respond to classical therapy.

3) Patients on PPI's for long periods of time appear to show some "rebound" acid secretion. This result could again be linked to the fundic $H^+$-ATPase, which we show is sensitive to Histamine and to the levels of protons within the cell.

In preferred embodiments of this invention aspect, a single zinc salt which is water-soluble regardless of pH (i.e., within a range of pH from about 1.0 to about 7.5 or above) is preferred. Zinc chloride is the preferred salt for use in the present invention. In alternative embodiments, a mixture of a low pH soluble zinc salt with a high pH soluble zinc salt or a zinc salt which may be readily absorbed through the small intestine (such as a zinc amino acid chelate compound), optionally in combination with a pharmaceutically acceptable buffer is provided. In this aspect of the invention, an effective amount of a zinc salt selected from the group consisting of zinc chloride ($ZnCl_2$), zinc acetate, zinc ascorbate, zinc succinate, zinc tartrate, zinc malate, zinc maleate, a zinc amino acid chelate (mono- or bis-chelate) and mixtures thereof, preferably a mixture of zinc chloride and at least one of zinc acetate, zinc gluconate, zinc succinate, zinc ascorbate, and a zinc amino acid chelate is provided alone or in combination with a pharmaceutically acceptable carrier, additive or excipient.

In various aspects, the present invention relates to the use of at least one water-soluble zinc salt alone or in combination with at least one compound/composition (within the context of the disease state or condition to be treated) selected from the group consisting of a traditional proton pump inhibitor compound/composition, an H2 blocker, an antibiotic/antimicrobial agent (effective against *H. pylori*), a cytoprotective agent or a mixture of these agents (Helidac, Prevpac) to provide fast action in reducing gastric acid secretion, to lower the pH of the stomach, to prevent or reduce the likelihood of ulcer disease, to treat ulcer disease, to treat gastric cancer, to treat a disease or condition selected from the group consisting of gastroesophageal reflux disease (GERD), non-erosive reflux disease (NERD), Zollinger-Ellison syndrome (ZE disease), ulcer disease, and gastric cancer, as well as preventing or reducing the likelihood of ulcer disease.

Pharmaceutical compositions comprising a mixture of zinc salts which maximize both immediate and extended release characteristics of the present invention, optionally in combination with a pharmaceutically acceptable carrier, additive or excipient and further optionally an effective amount of additional agent selected from the group consisting of a proton pump inhibitor, an $H_2$ blocker, an anti-*H. pylori* antibiotic/antimicrobial, a cytoprotective agent and a combination of agents, are additional aspects of the present invention. Any one or more of these compositions may be used within context to treat the various conditions/disease states as otherwise disclosed herein.

In an additional aspect of the present invention, pharmaceutical compositions comprise at least one water soluble zinc salt as otherwise described herein in combination with at least one (additional) therapeutic agent wherein the oral administration of said agent is favorably affected by elevated pH levels in the stomach, optionally in combination with a pharmaceutically acceptable carrier, additive or excipient. It has unexpectedly been discovered that the inclusion of a water soluble zinc salt as otherwise described herein to raise the pH of the gastric juices, in combination with a therapeutic agent which is favorably responsive to elevated pH levels because of the tendency of the agent to produce/increase undesired acidity in the stomach, because of acid sensitivity of the therapeutic agent, because of enhanced solubility at higher acid pH's (less acid) of about 3.5-4.0 or higher, and/or because of the tendency of the therapeutic agent to create GI tract distress or ulcerations at lower pH's, which are substantially reduced or alleviated at higher pH's represents a general approach for enhancing the oral administration of therapeutic agents by increasing bioavailability and/or decreasing the side effects from the therapeutic agent.

DETAILED DESCRIPTION OF THE INVENTION

The following terms are used throughout the specification to describe the present invention.

The term "patient" or "subject" refers to an animal, preferably a mammal, even more preferably a human, in need of treatment or therapy to which compounds according to the present invention are administered in order to treat a condition or disease state treatable using compounds according to the present invention. Depending upon the disease or condition treated the term patient refers to the animal treated for that disease within context.

The term "effective" is used to describe a treatment, compound, composition, component or a related aspect of the present invention, which, when used in context, produces an intended result which may include the increase in pH in the stomach, the reduction of symptoms associated with excess acid release, the enhanced bioavailability of an administered compound, or the favorable treatment of a disease state or condition. The term effective subsumes both an amount or concentration of one or more active agent(s) as described herein and a period of time which is consistent with producing an intended effect.

The term "pharmaceutically acceptable zinc salt" or zinc salt" used in context, refers \ to a salt or salt combination which contains zinc, dissolves in the gastric juices at reduced pH and is absorbed to some extent in the gastric mucosa at a low pH of about 2 or less, at a higher pH of about 4.0 to 5.0 or above of the stomach and at the high pH's of the small intestine to reach and maintain effective concentrations of zinc in the blood stream over a period of therapy. Exemplary pharmaceutically compatible zinc salts include both inorganic and organic zinc salts, for example, zinc acetate, zinc ascorbate, zinc benzoate, zinc bromide, zinc butyrate, zinc caprylate, zinc carbonate (soluble in dilute acid at low pH of the stomach), zinc carnosine, zinc citrate, zinc chloride, zinc fluoride, zinc formate, zinc fumarate, zinc fumaric acid monoethyl ester, zinc gallate, zinc gluconate, zinc glutarate, zinc glycerate, zinc glycerophosphate, zinc glycolate, zinc hydroxide, zinc iodide, zinc iodate, zinc lactate, zinc malate, zinc maleate, zinc myristate, zinc nitrate, zinc oratate, zinc oxide, zinc phenol sulfonate, zinc phosphate, zinc picolinate, zinc picrate, zinc propionate, zinc salicylate, zinc selenate, zinc stearate, zinc succinate, zinc sulfate, zinc tannate, zinc tartrate, zinc undecylenate, zinc valerate, and zinc chelates, including zinc amino acid chelates (including, depending on concentration, mono- and bis-chelates of L- or D-amino acids (preferably, the naturally occurring L-amino acid which may be more readily absorbed from the gastrointestinal tract) which complex or chelate with zinc including preferably, L-arginine (zinc arginate), L-cysteine, L-cystine, L-N-acetyl-cysteine, L-histidine (also D-histidine as zinc histidinate), L-taurine, L-glycinate, L-aspartate (zinc aspartate) and L-methionine (zinc methionine), among others. Note that for purposes of the present invention, zinc chelates, including zinc nicotinamide complex and zinc amino acid chelates are considered zinc salts. Preferred zinc salts for use in the present invention include zinc acetate, zinc arginate, zinc butyrate, zinc chloride, zinc citrate, zinc formate, zinc fumarate, zinc gluconate, zinc glutarate, zinc glycerate, zinc glycolate, zinc histidinate, zinc lactate, zinc malate, zinc maleate, zinc picolinate, zinc propionate, zinc salicylate, zinc succinate, zinc sulfate, zinc undecylenate, zinc salt of 1,6 fluctose diphosphate and mixtures thereof.

Preferably, the pharmaceutically acceptable zinc salt is "water soluble". The term "water soluble" is used to describe a zinc salt (and zinc chelates which fall under this term) according to the present invention which has a water solubility of at least about 0.01 moles/Liter, preferably at least about 0.05 moles/Liter.

One of ordinary skill will recognize favorable zinc salts to use in the present invention. In aspects of the invention, at least one pharmaceutically compatible, water-soluble zinc salt is administered to a patient in order to provide a rapid inhibition of acid release in the stomach, resulting in an increase in stomach pH to above 4 (generally between about 4.0 and 5.0, in some cases above 5.0) for an extended period of time, preferably at least 2 hours, 4 hours, 6 hours, 8 hours, 10 hours, 12 hours, 16 hours, 20 hours or more. It is noted that in certain preferred aspects of the invention, the zinc salt or combination of salts chosen to be administered to the patient may be adjusted to provide an initial bolus concentration of zinc in the stomach at low pH in order to produce the rapid inhibition of acid release and rise in pH in the stomach to a level above about 4. In addition, a preferred zinc salt or salt combination inhibits acid release in the stomach at varying levels of acidity and pH—i.e., at a level which is quit acidic (pH, less than about 2.0) to a pH of about 4.0 or higher.

The term "providing fast action in reducing gastric acid secretion" is used to describe the fact that the method according to the present invention results in an increase in pH to a level of at least about 4.0, more preferably about 4.0 to about 5.0 or slightly above, in a period of no greater than about 30 minutes, preferably in less than about 20-30 minutes, even more preferably in less than about 10-20 minutes, in about 15 minutes or less or alternatively, in less than about 5 minutes.

The term "secretagogue" refers to the period during which time the pariental cells of the stomach secrete acid into the gastric juices to lower pH. Often the secretagogue period occurs just after a meal, but the secretion of acid may occur at other times. The secretagogue phase can be of short duration or longer duration.

The term gastroesophageal reflux disease or "GERD" or "acid reflux" is a condition in which the liquid content of the stomach regurgitates (backs up, or refluxes) into the esophagus. The liquid can inflame and damage the lining of the esophagus although this occurs in a minority of patients. The regurgitated liquid usually contains acid and pepsin that are produced by the stomach. The refluxed liquid also may contain bile that has backed-up into the stomach from the duodenum. Acid is believed to be the most injurious component of the refluxed liquid. Pepsin and bile also may injure the esophagus, but their role in the production of esophageal inflammation and damage (esophagitis) is not as clear as is the role of acid.

GERD is a chronic condition. Once it begins, it usually is life-long. If there is injury to the lining of the esophagus (esophagitis), this also is a chronic condition. Moreover, after the esophagus has healed with treatment and treatment is stopped, the injury will return in most patients within a few months. Once treatment for GERD is begun, therefore, it may be necessary to continue the treatment continually, generally for short periods of time.

Actually, the reflux of the stomach's liquid contents into the esophagus occurs in most normal individuals. In fact, one study found that reflux occurs as frequently in normal individuals as in patients with GERD. In patients with GERD, however, the refluxed liquid contains acid more often, and the acid remains in the esophagus longer.

Gravity, swallowing, and saliva are important protective mechanisms for the esophagus, but they are effective only when individuals are in the upright position. At night while sleeping, gravity is not in effect, swallowing stops, and the secretion of saliva is reduced. Therefore, reflux that occurs at night is more likely to result in acid remaining in the esophagus longer and causing greater damage to the esophagus.

Certain conditions make a person susceptible to GERD. For example, reflux can be a serious problem during pregnancy. The elevated hormone levels of pregnancy probably cause reflux by lowering the pressure in the lower esophageal sphincter (see below). At the same time, the growing fetus increases the pressure in the abdomen. Both of these effects would be expected to increase reflux. Also, patients with diseases that weaken the esophageal muscles (see below), such as scleroderma or mixed connective tissue diseases, are more prone to develop reflux.

The cause of GERD is complex. There probably are multiple causes, and different causes may be operative in different individuals or even in the same individual at various times.

A number of patients with GERD produce abnormally large amounts of acid, but this is uncommon and not a contributing factor in the vast majority of patients. The factors that contribute to causing GERD are the lower esophageal sphincter, hiatal hernias, esophageal contractions, and emptying of the stomach. Notwithstanding the cause of GERD, the present invention may reduce the tendency of having injurious acid reflux into the esophagus, causing damage.

When the wave of contraction in the esophagus is defective, refluxed acid is not pushed back into the stomach. In patients with GERD, several abnormalities of contraction have been described. For example, waves of contraction may not begin after each swallow or the waves of contraction may die out before they reach the stomach. Also, the pressure generated by the contractions may be too weak to push the acid back into the stomach. Such abnormalities of contraction, which reduce the clearance of acid from the esophagus, are found frequently in patients with GERD. In fact, they are found most frequently in those patients with the most severe GERD. The effects of abnormal esophageal contractions would be expected to be worse at night when gravity is not helping to return refluxed acid to the stomach. Note that smoking also substantially reduces the clearance of acid from the esophagus. This effect continues for at least 6 hours after the last cigarette.

Most reflux during the day occurs after meals. This reflux probably is due to transient LES relaxations that are caused by distention of the stomach with food. A minority of patients with GERD, about 20%, has been found to have stomachs that empty abnormally slowly after a meal. The slower emptying of the stomach prolongs the distention of the stomach with food after meals. Therefore, the slower emptying prolongs the period of time during which reflux is more likely to occur.

The term "non-erosive reflux disease" or "NERD" is used describe a specific form of GERD, described above. In some cases, GERD erodes the esophageal lining, creating a condition called esophagitis. NERD is GERD that does not cause esophagitis. Because most GERD sufferers do not have esophagitis, NERD is the most common form of GERD. Because its name contains the word "nonerosive," it may appear that NERD is the least severe form of GERD, but this is not necessarily so. NERD is actually more likely to produce extra-esophageal complications, and is also less likely to respond to fundoplication surgery. In one study, only 56% of NERD patients (compared with 90% of patients with erosive reflux) reported that their symptoms were completely eliminated with fundoplication. NERD was also twice as likely to cause swallowing difficulties.

Heartburn is the chief symptom of NERD. It has a number of potential causes, including hiatal hernia, lifestyle behaviors, and diet. Many people deal with heartburn by simply adjusting their behavior. In some cases, medication or surgery may be required. Traditional antacids have also been used to treat NERD.

The term "Zollinger-Ellison syndrome" or "ZE syndrome" is used throughout the specification to describe a condition caused by abnormal production of the hormone gastrin. In ZE syndrome, small tumor (gastinoma) in the pancreas or small intestine produces the high levels of gastrin in the blood. ZE syndrome is caused by tumors usually found in the head of the pancreas and the upper small bowel. These tumors produce the hormone gastrin and are called gastrinomas. High levels of gastrin cause overproduction of stomach acid. High stomach acid levels lead to multiple ulcers in the stomach and small bowel. Patients with ZE syndrome may experience abdominal pain and diarrhea. The diagnosis is also suspected in patients without symptoms who have severe ulceration of the stomach and small bowel.

The agents of choice for treating ZE syndrome are the proton pump inhibitors (PPI) as described hereinabove. These drugs dramatically reduce acid production by the stomach, and promote healing of ulcers in the stomach and small bowel. They also provide relief of abdominal pain and diarrhea.

Surgical removal of a single gastrinoma may be attempted if there is no evidence that it has spread to other organs (such as lymph nodes or the liver). Surgery on the stomach (gastrectomy) to control acid production is rarely necessary today. Early diagnosis and surgical removal of the tumor is associated with a cure rate of only 20% to 25%. However, gastrinomas grow slowly, and patients may live for many years after the tumor is discovered. Acid-suppressing medications are very effective at controlling the symptoms of acid overproduction.

The term "ulcer" is used throughout the specification to describe an area of tissue erosion, for example, especially of the lining of the gastrointestinal (GI) tract, especially of the stomach (peptic ulcer), esophagus or small intestine (duodenal ulcer). Due to the erosion, an ulcer is concave. It is always depressed below the level of the surrounding tissue. Ulcers can have diverse causes, but in the GI tract, they are believed to be primarily due to infection with the bacteria *H. pyloridus* (*h. pylori*). GI ulcers, however, may be made worse by stress, smoking and other noninfectious factors, especially including excessive stomach acid because a lower pH tends to be a better growth environment for *H. Pyloridus*.

Traditional treatments for *H. pyloridus* infections include antimicrobials/antibiotics, such as amoxicillin, clarithromycin (biaxin), metronidazole (flagyl) and tetracycline ("an anti-*H. pylori* agent"); $H_2$-blockers, such as cimetidine (tagamet), famotidine (pepcid), nizatidine (axid), ranitidine (zantac); proton pump inhibitors (PPI), such as esomeprazole (nexium), lansoprazole (prevacid), omeprazole (prilosec), pantoprazole (protonix) and rabeprazole (aciphex); cytoprotective agents, such as bismuth subsalicylate, sucralfate; and combination agents, such as Helidac (bismuth subsalicylate, metronidazole, and tetracycline combination), Prevpac (lansoprazole, clarithromycin and amoxicillin).

The present invention may be used to treat an *H. pyloridus* infection in a patient by administering an effective amount of at least one pharmaceutically acceptable water-soluble zinc salt, either alone or in combination (preferably, by coadministration) with at least one other of the traditional treatment modalities, as described above.

The term "coadministration" or "combination therapy" is used to describe a therapy in which at least two active compounds in effective amounts are used to treat one or more of the disease states or conditions as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. The active compositions may include one or more zinc salts and/or additional compounds/compositions such as proton pump inhibitors, $H_2$ blockers, antibiotics/antimicrobial agents, cytoprotective agents or combination agents as otherwise described herein in effective amounts for the disease or condition for which the compounds are typically used. In addition, coadministration also contemplates combinations of water soluble zinc salts as otherwise described herein in combination with at least one therapeutic agent wherein elevated pH levels provide a favorably response to the administration of said therapeutic agent.

The term "favorably responsive to elevated pH levels" or "favorably orally administered" is used to describe therapeutic agents which, in orally administered compositions, provide a favorable response to an elevated pH in the stomach produced by a water soluble zinc salt according to the present invention, whether that favorable response is a reduction in gastric irritation from the therapeutic agent, a reduction in acid generation/production in the stomach by the therapeutic agent, to increase bioavailability which is negatively impacted by the sensitivity and/or inactivation of the therapeutic agent to an acidic environment or because of increased solubility of the therapeutic agent in gastric juices at high pH levels. It has unexpectedly been discovered that the inclusion of a water soluble zinc salt as otherwise described herein, in combination with a therapeutic agent which is favorably responsive to elevated pH levels because of the tendency of the agent to increase acid release and a lowering of pH in the stomach, because of increased acid sensitivity of the therapeutic agent, because of enhanced solubility of the agent (with concombinant increased bioavailability of the therapeutic agent) at higher (less acid) pH's of about 3.5-4.0 or higher, and/or because of the tendency of the therapeutic agent to create GI tract distress or ulcerations at lower pH's, which are substantially reduced or alleviated at higher pH's results in greater activity and/or fewer side effects from the therapeutic agent.

In general, the weight ratio of water soluble zinc salt to therapeutic agent which is included in combination therapeutic compositions according to the present invention ranges from about 1:20 to about 20:1, about 1:10 to about 10:1, about 1:5 to about 5:1, about 1:3 to about 3:1, about 1:2 to about 2:1, about 1:1.5 to about 1.5 to 1, about 1:1. Of course, the weight ratio used in a particular combination pharmaceutical composition will depend upon the water solubility of the zinc salt and the activity of the therapeutic agent in producing a side effect (such as increasing stomach acid or increasing gastrointestinal distress (GI tract distress) or the tendency to increase the environment for ulceration in the gastrointestinal tract), or to be inactivated, rendered insoluble or have its bioavailability negatively impacted by stomach acid, etc.

Therapeutic compounds which may be favorably administered orally (for the reasons which are outlined above) in combination with a water soluble zinc salt in the present invention include the following:

Chemotherapeutic Agents

Zn plus chemolitic agents for use in treating intestinal cancer e.g., Cysplatine;

Zn plus chemolitic agents used to treat whole tissue cancer with secondary complications in the intestinal track (GI tract distress) as follows:

13-cis-Retinoic Acid;
2-CdA (2-Chlorodeoxyadenosine);
5-Azacitidine;
5-Fluorouracil (5-FU);
6-Mercaptopurine (6-MP);
6-TG (6-Thioguanine);
Abraxane;
Accutane® (Isotretinoin);
Actinomycin-D;
Adriamycin® (Doxorubicin Hydrochloride);
Adrucil® (Fluorouracil);
Agrylin® (Anagrelide);
Ala-Cort® (Hydrocortisone);
Aldesleukin;

Alemtuzumab;
ALIMTA (Pemetrexed);
Alitretinoin;
Alkaban-AQ® (Vinblastine);
Alkeran® (Melphalan);
All-transretinoic Acid;
Alpha Interferon;
Altretamine;
Amethopterin;
Amifostine;
Aminoglutethimide;
Anagrelide;
Kidrolase® (Asparaginase);
Lanacort® (Hydrocortone Phosphate);
L-asparaginase;
LCR (Leurocristine);
Lenalidomide;
Letrozole;
Leucovorin;
Leukeran;
Leukine™ (Sargramostim);
Leuprolide;
Leurocristine;
Leustatin™ (Cladribin);
Liposomal Ara-C;
Liquid Pred® (Deltasone);
Lomustine;
L-PAM (L-phenylalanine mustard, phenylalanine mustard);
L-Sarcolysin;
Lupron® (Leuprolide Acetate Inj);
Lupron Depot® (Leuploride Acetate);
Matulane® (Procarbazine);
Maxidex;
Mechlorethamine;
Mechlorethamine Hydrochloride;
Medralone® (Methylprednisolone);
Medrol® (Methylprednisolone);
Megace® (Megestrol Acetate);
Megestrol;
Megestrol Acetate;
Melphalan;
Mercaptopurine;
Mesna;
Mesnex™ (Mesna);
Methotrexate;
Anandron® (Nilutamide);
Anastrozole
Arabinosylcytosine;
Ara-C;
Aranesp® (Darbepoetin Alfa);
Aredia® (Pamidronate);
Arimidex® (Anastrozole);
Aromasin® (Exemestane);
Arranon® (Nelarabine);
Arsenic Trioxide;
Asparaginase;
ATRA (Atragen);
Avastin® (Bevacizumab);
Azacitidine;
BCG (Bacillus Calmette Guerin);
BCNU (Carmustine);
Bevacizumab;
Bexarotene;
BEXXAR® (Tositumomab and Iodine 1131 Tositumomab);
Bicalutamide;
BiCNU (CARMUSTINE);
Blenoxane® (Bleomycin Sulfate);
Bleomycin;
Bortezomib;
Busulfan;
Busulfex® (Busuflan);
C225 (Eribitux);
Calcium Leucovorin;
Campath® (Alemtuzumab;
Camptosar® (Irinotecan hydrochloride);
Camptothecin-11;
Capecitabine;
Carac™ (Fluorouracil);
Carboplatin;
Carmustine;
Carmustine Wafer;
Casodex® (Bicalutamide);
CC-5013 (Revlimid);
CCNU (lomustine);
CDDP (Cisplatin);
CeeNU;
Cerubidine® (Daunorubicin);
Cetuximab;
Chlorambucil;
Cisplatin;
Methotrexate Sodium;
Methylprednisolone;
Meticorten® (prednisone);
Mitomycin;
Mitomycin-C;
Mitoxantrone;
M-Prednisol® (Methlyprednisolone);
MTC (Mitomycin);
MTX (Methotrexate);
Mustargen® (Mechlorethamine HCl);
Mustine;
Mutamycin® (Mitomycin);
Myleran® (Busulfan);
Mylocel™ (Hydroxyurea);
Mylotarg® (Gemtuzumab Ozogamicin);
Navelbine® (Vinorelbine Tartrate);
Nelarabine
Neosar® (Cyclophosphamide);
Neulasta™ (Pegfilgrastim);
Neumega® (Oprelvekin);
Neupogen® (Filgrastim);
Nexavar® (Sorafenib);
Nilandron® (Nilutamide);
Nilutamide;
Nipent® (Pentostatin);
Nitrogen Mustard;
Novaldex® (Genox);
Novantrone® (Mitoxantrone);
Octreotide;
Octreotide acetate;
Oncospar® (Pegylated asparaginase);
Oncovin® (Vincristine Sulfate);
Ontak® (Denileukin Diftitox);
Onxal™ (Paclitaxel);
Oprevelkin;
Orapred® (Prednisolone Sodium Phosphate);
Orasone® (prednisone);
Oxaliplatin;
Paclitaxel;
Paclitaxel Protein-bound;
Pamidronate;

Panitumumab;
Panretin® (Alitretinoin);
Paraplatin® (Paraplatin);
Citrovorum Factor;
Cladribine;
Cortisone;
Cosmegen® (Dactinomycin);
CPT-11 (Topotecan);
Cyclophosphamide;
Cytadren® (Aminoglutethimide);
Cytarabine;
Cytarabine Liposomal;
Cytosar-U® (Cytarabine);
Cytoxan® (Cyclophosphamide);
Dacarbazine;
Dacogen;
Dactinomycin;
Darbepoetin Alfa;
Dasatinib;
Daunomycin;
Daunorubicin;
Daunorubicin Hydrochloride;
Daunorubicin Liposomal;
DaunoXome® (Daunorubicin Liposoma);
Decadron;
Decitabine;
Delta-Cortef® (Prednisolone);
Deltasone® (Prednisone);
Denileukin diftitox;
DepoCyt™ (Cytarabine liposome injection);
Dexamethasone;
Dexamethasone acetate;
Dexamethasone Sodium Phosphate;
Dexasone;
Dexrazoxane;
DHAD (Novantrone);
DIC (Disseminated intravascular coagulation);
Diodex;
Docetaxel;
Doxil® (Doxorubicin HCl liposome);
Doxorubicin;
Doxorubicin liposomal;
Droxia™ (Hydroxyurea);
DTIC (Dacarbazine);
DTIC-Dome® (dacarbazine);
Duralone®;
Efudex® (fluorouracil topical);
Eligard™ (Leuprolide Acetate);
Pediapred® (Prednisolone Sodium);
PEG Interferon;
Pegaspargase;
Pegfilgrastim;
PEG-INTRON™ (Peginterferon alfa-2b);
PEG-L-asparaginase;
PEMETREXED;
Pentostatin;
Phenylalanine Mustard;
Platinol® (Cisplatin);
Platinol-AQ® (Cisplatin);
Prednisolone;
Prednisone;
Prelone® (Prednisolone);
Procarbazine;
PROCRIT® (Epoetin Alfa);
Proleukin® (Aldesleukin);
Prolifeprospan 20 with Carmustine;
Implant;
Purinethol® (Mercaptopurine);
Raloxifene;
Revlimid® (Lenalidomide);
Rheumatrex® (Trexall);
Rituxan® (Rituximab);
Rituximab;
Roferon-A® (Interferon Alfa-2a);
Rubex® (adriamycin)
Rubidomycin hydrochloride;
Sandostatin® (Octreotide Acetate);
Sandostatin LAR® (Octreotide Acetate inj);
Sargramostim;
Solu-Cortef® (Hydrocortisone Sodium Succinate);
Solu-Medrol® (Methylprednisolone sodium succinate);
Sorafenib;
SPRYCEL™ (Dasatinib);
STI-571 (Gleevec);
Streptozocin;
SU11248;
Sunitinib;
Sutent® (Sunitinib Malate);
Tamoxifen;
Tarceva® (Erlotinib);
Targretin® (Bexarotene);
Taxol® (Paclitaxel);
Ellence™ (Epirubicin hydrochloride);
Eloxatin™ (Oxaliplatin Inj);
Elspar® (Asparaginase);
Emcyt® (Estramustine);
Epirubicin;
Epoetin alfa;
Erbitux™ (Cetuximab);
Erlotinib;
Erwinia L-asparaginase;
Estramustine;
Ethyol;
Etopophos® (Etoposide Phosphate);
Etoposide;
Etoposide Phosphate;
Eulexin® (Flutamide);
Evista® (Raloxifene);
Exemestane;
Fareston® (Toremifene);
Faslodex® (Fulvestrant);
Femara® (Letrozole);
Filgrastim;
Floxuridine;
Fludara® (Fludarabine);
Fludarabine;
Fluoroplex® (Fluorouracil topical);
Fluorouracil;
Fluorouracil (cream);
Fluoxymesterone;
Flutamide;
Folinic Acid;
FUDR® (Floxuridine);
Fulvestrant;
G-CSF (Neupogen);
Gefitinib;
Gemcitabine;
Gemtuzumab ozogamicin;
Gemzar® (Gemcitabine);
Gleevec™;
Gliadel® (Carmustine Wafer);
GM-CSF;
Goserelin;
Granulocyte—Colony Stimulating Factor;

Granulocyte Macrophage Colony Stimulating Factor;
Taxotere® (Docetaxel);
Temodar® (Temozolomide);
Temozolomide;
Teniposide;
TESPA (Thiotepa);
Thalidomide;
Thalomid® (Thalidomide);
TheraCys® (Intravesical);
Thioguanine;
Thioguanine Tabloid® (Thioguanine);
Thiophosphoamide;
Thioplex® (Thiotepa);
Thiotepa;
TICE® (Bacillus of Calmette and Guerin);
Toposar® (Etoposide);
Topotecan;
Toremifene;
Tositumomab;
Trastuzumab;
Tretinoin;
Trexall™ (Methotrexate);
Trisenox® (Arsenic);
TSPA (Thiotepa);
VCR;
Vectibix™ (Panitumumab);
Velban® (Vinblastine Sulfate);
Velcade® (Bortezomib);
VePesid® (Etoposide);
Vesanoid® (Tretinoin);
Viadur™ (Leuprolide Acetate Implant);
Vidaza® (Azacitidine);
Vinblastine;
Vinblastine Sulfate;
Vincasar Pfs® (Vincristine Sulfate Injection);
Vincristine;
Vinorelbine;
Vinorelbine tartrate;
VLB (Vinblastine Sulfate);
VM-26;
Vorinostat;
VP-16 (Etoposide);
Vumon® (Teniposide);
Xeloda® (Capecitabine);
Zanosar® (Streptozocin);
Halotestin® (Fluoxymesterone);
Herceptin® (Trastuzumab);
Hexadrol;
Hexalen® (Altretamin);
Hexamethylmelamine;
HMM (antineoplastic or cytotoxic);
Hycamtin® (Hycamtin);
Hydrea® (Hydroxyurea);
Hydrocort Acetate® (Hydrocortisone);
Hydrocortisone;
Hydrocortisone Sodium Phosphate;
Hydrocortisone Sodium Succinate;
Hydrocortone Phosphate;
Hydroxyurea;
Ibritumomab;
Ibritumomab Tiuxetan;
Idamycin® (Idarubicin);
Idarubicin;
Ifex® (Ifosfamide);
IFN-alpha;
Ifosfamide;
IL-11;
IL-2;
Imatinib mesylate;
Imidazole Carboxamide;
Interferon alfa;
Interferon Alfa-2b (PEG Conjugate);
Interleukin-2;
Interleukin-11;
Intron A® (interferon alfa-2b);
Iressa® (Getfitinib);
Irinotecan;
Isotretinoin;
Zevalin™;
Zinecard® (Dexrazoxane);
Zoladex® (Goserelin);
Zoledronic acid;
Zolinza;
Zometa® (Zoledronic Acid for Inj).

Immunosuppression Agents

Zn plus agents used as immunosuppressive agents following organ transplantation such as cyclosporine and its derivatives, azathioprine, 6-mercaptopurine, Prednisone, infliximab (Remicade), and tetracycline, among others.

Assorted Medications

Zn given in combination with asthma related drugs: Theophylline and cortisteroids, including betamethasone, cortisone, dexamethasone, hydrocortisone, methylprednisolone, prednisolone and budenoise. Each of these agents can induce stomach lining erosion and increased acid secretion.

NSAIDS:

Over the counter NSAIDS and associated compounds cause GERD and GERD symptoms including ulcer disease:

| OTC Name | Generic Name |
| --- | --- |
| Actron ® | ketoprofen |
| Advil ® | ibuprofen |
| Aleve ® | naproxen sodium |
| Bayer ® | aspirin |
| Ecotrin ® | aspirin |
| Excedrin ® | aspirin, acetaminophen and caffeine |
| Motrin IB ® | ibuprofen |
| Nuprin ® | ibuprofen |
| Orudis KT ® | ketoprofen |

Antidepressive Agents

Selective serotonin reuptake inhibitors (SSRIs): Citalopram (Celexa), Escitalopram (Lexapro), Fluoxetine (Prozac); Parozxetine (Paxel) and Sertraline (Zoloft.)

Zn taken in combination with the following drugs could potentially increase bioavailability of molecule due to the fact zinc does not cause the effects on inhibiting Cytochromes P-450 2C9 & 3A4 as omeprazole or esoprazole.

Carbamazepine;
Cyclosporine;
Diazepam, other benzodiazepines;
Diltiazem, Nifedipine, Verapamil;
Erythromycin, Clarithromycin;
Lidocaine;
Lovastatin, other statins including Atorvastatin,
Phenytoin;
Quinidine;
Terfenadine The term "proton pump inhibitor" is used throughout the specification to describe Proton pump inhibitors as drugs that help control the painful discomfort of heartburn and gastroesophageal reflux disease (GERD), and promote the healing of stomach and duodenal ulcers. Proton pump inhibitors are only available by prescription. They come as tablets, capsules, injections, or powders that are made into a suspension.

Proton inhibitors work by blocking the production of stomach acid. They inhibit a system in the stomach known as the proton pump, which is another name for the "hydrogen-potassium adenosine triphosphate enzyme" system. Proton pump inhibitors are rather versatile. They are used to heal stomach and duodenal ulcers, including stomach ulcers caused by taking nonsteroidal anti-inflammatory drugs. They are also used to relieve symptoms of oesophagitis (inflammation of the oesophagus or gullet) and severe gastroesophageal reflux (GERD), as discussed above.

Combined with certain antibiotics (such as amoxycillin and clarithromycin) or with zinc salts according to the present invention, proton pump inhibitors are effective for treating *Helicobacter pylori* infections (a bacterial infection of the stomach). The *H. pylori* bacterium is a chief suspect in the cause of recurring stomach ulcers. PPIs are also a first-choice treatment for the rare condition called Zollinger-Ellison syndrome, discussed above.

Proton Pump Inhibitors exhibit side effects, although they tend to be manageable, including diarrhea, feeling or being sick, constipation, flatulence, abdominal pain, headaches and more rarely, allergic reactions, itching, dizziness, swollen ankles, muscle and joint pain, blurred vision, depression and dry mouth, among others. Long-term use of proton pump inhibitors can result in stomach infections. Because proton pump inhibitors completely stop acid production—and stomach acid helps kill microbes such as bacteria in the stomach—using PPIs can lead to growth of potentially harmful microbes in the stomach.

Proton pump inhibitors exhibit significant, sometimes deleterious drug interactions, including reactions with phenytoin as an epilepsy agent and warfarin to prevent blood clots, to increase their effects, with ketoconazole and itraconazole to reduce their absorptivity, with diazepam (valium) to decrease its metabolism.

Proton pump inhibitors are usually taken for 1-2 months, but in some cases may be taken longer. Symptoms may return when a person stops taking a proton pump inhibitor. Proton pump inhibitors may cause internal bleeding, signs of which include vomiting blood, detecting a substance-like coffee grounds in your vomit, or pass black tarry stools, see your doctor immediately.

Common proton pump inhibitors include omeprazole (Prilosec), esomeprazole (Nexium), lansoprazole (Prevacid), pantoprazole (Protonix) and rabeprazole sodium (Aciphex).

The present invention relates to a method for providing fast action with optional long duration effect in reducing gastric acid secretion, raising the pH of the stomach during a resting phase, decreasing the duration of stomach acid release during a secretagogue phase and for treating conditions including gastroesophageal reflux disease (GERD), non-erosive reflux disease (NERD), Zollinger-Ellison syndrome (ZE disease), ulcer disease, and gastric cancer where the reduction in gastric acid secretion is beneficial, as well as preventing or reducing the likelihood of ulcer disease by reducing gastric acid section. In addition, the present methods are useful for treating patients who are non-responsive to proton pump inhibitors (PPI) and as an alternative to traditional therapies or conditions which are caused by rapid and complete inhibition of secretagogue induced acid secretion.

The method comprises administering an effective amount of at least one pharmaceutically acceptable water-soluble zinc salt to alleviate or treat the condition or disease state. The methods may involve the administration of a water-soluble zinc salt alone or in combination with other agents as disclosed herein a single time, or preferably for longer duration, usually about 2-3 days to about 2-3 months, with varying intervals in between, depending upon the prognosis and outcome of the treatment.

Zinc salts according to the present invention may be administered alone or in combination with other compounds, compositions or therapies, depending upon the condition or disease state to be treated, including an effective amount of a proton pump inhibitor or other agent as otherwise described herein which may be used to treat *H. pylori* infections. These agents include proton pump inhibitors such as esomeprazole, lansoprazole, omeprazole, pantoprazole or rabeprazole, H2 blockers such as cimetidine, famotidine, nizatidine or ranitidine, anti-*H. pylori* agents, such amoxicillin, clarithromycin (biaxin), metronidazole (flagyl) or tetracycline, cytoprotective agents such as bismuth subsalicylate or sucralfate, or a combination agent such as Helidac or Prevpac.

In a preferred aspect of the invention, at least one water-soluble zinc salt is used wherein the zinc salt or combination is characterized as being soluble and absorbable (through the gastrointestinal mucosa) at both low pH (i.e., a pH of about 1-2, which occurs in an acidic condition in the stomach) and higher pH (i.e., a pH of about 4-5 or slightly above after acid secretion in the stomach is inhibited or even higher—i.e., a pH of about 5.5-6.0 in the duodenum to about 6.5-7.5 in the jejunum and ileum—the pH is slightly higher in the ileum than in the jejunum). By providing for compositions which are both water-soluble and absorbable throughout the gastrointestinal mucosa (i.e. in the stomach and through the various sections of the small intestine), the bioavailability of the zinc salt will be maximized as will favorable therapy of the conditions or disease states to be treated. In this aspect, a preferred combination of effective amounts of zinc chloride and at least one zinc salt preferably selected from the group consisting of zinc acetate, zinc arginate, zinc butyrate, zinc citrate, zinc formate, zinc fumarate, zinc gluconate, zinc glutarate, zinc glycerate, zinc glycolate, zinc histidinate, zinc lactate, zinc malate, zinc maleate, zinc picolinate, zinc propionate, zinc salicylate, zinc succinate, zinc sulfate, zinc undecylenate, zinc salt of 1,6 fluctose diphosphate and mixtures thereof, more preferably, zinc acetate, zinc gluconate, zinc ascorbate, zinc succinate and a zinc amino acid chelate (as mono- or bis-amino acid chelate) is preferred, although numerous other zinc acid compounds may be combined to produce favorable results.

Preferred zinc salts include those salts in which the anionic counterion in protonated form has a pKa of at least about 4 to about 5.5 or higher. Mixtures of zinc salts wherein all of the zinc salts are soluble within a range of pH from 1-2 to about 7.5 are preferred. Zinc acetate, zinc gluconate, zinc glycolate, zinc succinate and zinc ascorbate alone or in combination with another zinc salt, especially zinc chloride, are particularly useful for use in the present invention. Zinc chelates, especially zinc amino acid chelates (mono- or bis-amino acid chelates) may also be preferably used wherein a combination of zinc chloride and a zinc amino acid chelate selected from the group consisting of zinc chelates (mono- or bis-chelates) of L-cysteine, L-cystine, L-N-acetylcysteine, L-histidine, D-histidine, L-taurine, L-glycinate, L-aspartate, L-methionine, and mixtures thereof.

Note that the following zinc salts have solubilities which tend to be reduced at pH values above about 7.0, so approaches to formulation should accommodate such information where absorptivity from the small intestine is featured (duodenum, jejunum and ileum), especially at the distil end (jejunum, ileum) where the pH of the small intestine may rise to between 7-8.0. Note that the use of such salts may favorably influence release characteristics of formulations and provide a means of delivering therapeutic agents, especially those which are administered in combination therapy according to the present invention. Zinc salts that become insoluble above a pH of 7 include zinc acetate, zinc chloride, zinc bromide, zinc fluoride, zinc iodide, zinc sulfate, zinc citrate, zinc lactate, zinc nitrate, zinc propionate, zinc salicylate, zinc tartrate, zinc valerate, zinc gluconate, zinc selenate, zinc benzoate, zinc formate, zinc glycerophosphate, zinc picrate, zinc butyrate, and the like, and combinations thereof.

Preferred zinc salts according to the invention include zinc chloride (where pKa of the counterion is not important because of its interaction with chloride channels) and organic acids including zinc acetate (pka 4.75), zinc gluconate, zinc succinate, zinc tartrate, zinc malate, zinc maleate, zinc zinc ascorbate (pka of 4.2 and 11.6). Other zinc salts of organic acids may also be preferred, depending on context of use. In addition, zinc glycolate and zinc lactate may also be used preferably, zinc glycolate being preferred. Other preferred salts include, for example, zinc acetate, zinc arginate, zinc butyrate, zinc chloride, zinc citrate, zinc formate, zinc fumarate, zinc gluconate, zinc glutarate, zinc glycerate, zinc glycolate, zinc histidinate, zinc lactate, zinc malate, zinc maleate, zinc picolinate, zinc propionate, zinc salicylate, zinc succinate, zinc sulfate, zinc undecylenate, zinc salt of 1,6 fluctose diphosphate and mixtures thereof. In aspects of the invention, it is preferred that when a combination of zinc salts is used that at least one zinc salt which is effective at low pH in the stomach (for immediate inhibition of acid secretion) be combined with an agent which may exhibit a heightened effect in the stomach at a pH of 4.0-5.0 or higher, or which is preferentially absorbed in the small intestine (a zinc mono- or bis-amino acid chelate or other chelate).

While not being limited by way of theory, it is believed that a combination of a zinc salt which is effective at low pH in the stomach (such as zinc chloride and also zinc sulfate) and one or more of the organic acid zinc salts as otherwise disclosed herein which are effective at a higher pH, will maximize delivery of zinc to the stomach mucosa to obtain a favorable effect, at first by being dissolved in acid gastric juice in the stomach where an initial inhibition of acid occurs and the pH rises, and subsequently, through absorption of zinc (from a zinc salt) at a higher pH in the stomach or in the small intestine where blood levels of zinc will increase to therapeutic levels. The absorption and effect of a zinc salt at higher pH levels in the stomach or at the higher pH of the small intestine (5.5-7.5 or higher) is advantageous because this delayed absorption of zinc will reduce gastric acid secretion at a later time (than an initial effect at a low pH) over an extended period of time. Compositions according to the present invention may be administered a single time, but usually are administered preferably once or twice daily orally for a period ranging from about 2-3 days to several months or longer.

Compositions according to the present invention also relate to sustained or extended release formulations which comprise a first component which allows or facilitates fast dissolution in the gastric juices at low pH so that a rapid inhibition of acid secretion is effected (with concominant increase in pH to a level of about 4.0 to about 5.0 or higher) and a second component which releases zinc salt at the higher pH level in the stomach or more preferably, further in the small intestine on a sustained release basis in order to maintain an effective level of zinc in the blood stream to inhibit gastric acid secretion in the stomach for extended periods. The first fast-acting component may be readily formulated using a zinc salt which dissolves in gastric juice at low pH (e.g., zinc chloride or zinc sulfate at a pH about 1.0 to about 2.0) using standard excipients such as lactose, confectioner's sugar in powered form, various stearate salts, etc, which dissolves rapidly in the stomach and a second sustained or extended release formulation which makes us of any number of polymeric binders, matrices (polymeric and/or erodible), granules, or enteric coatings to allow release of zinc salt on an extended or sustained release basis in the small intestine. Many of these techniques are well known in the art. Exemplary patents such as U.S. Pat. No. 4,863,741 to Becker, U.S. Pat. No. 4,938,967 to Newton, et al., U.S. Pat. No. 4,940,556 to MacFarlane, et al., and U.S. Pat. No. 5,202,128 to Morella, et al., among numerous others, may be useful for providing teachings, all well known in the art, for formulating fast release/sustained or extended release formulations useful in the present invention.

The above formulations may be useful for providing enhanced bioavailabity of one or more zinc salts and optionally, other agents which may be useful in treating or reducing the likelihood of one or more of gastric ulcers, GERD, NERD, Zollinger-Ellison syndrome, gastric cancer and reducing/inhibiting the secretion of acid in the stomach and raising the pH of the stomach to about 4.0 to about 5.0 or more, as otherwise disclosed in the present invention. It is noted that in inhibiting acid secretion in the stomach, blood concentrations of zinc salt of about 100 micromolar (µmol) produce inhibition of about 70%. With 300 µmol concentration of zinc salt, the inhibition approaches 100%. The time of action of inhibition from the blood delivery side at 100 µmol or 300 µmol is immediate (i.e., as soon as the zinc salt comes into contact with the cell membrane, inhibition occurs. It may be shown that inhibition occurs within about 10-15 minutes to 1 about hour in the presence of secretagogue. The zinc salts may be administered orally (preferably no more than once or twice a day) or intravenously, alone or in combination with optional PPI drugs.

The use of zinc chloride alone, or in combination with at least one additional zinc salt as otherwise described herein is preferred. Additional preferred zinc salts include zinc acetate, zinc gluconate, zinc ascorbate, zinc succinate, and zinc amino acid chelates (mono- and bis-amino acid chelates). These zinc salts and combinations may be used alone or in combination with additional agents such as a proton pump inhibitor (esomeprazole, lansoprazole, omeprazole, pantoprazole or rabeprazole), an H2 blocker (cimetidine, famotidine, nizatidine or ranitidine), an anti-*H. pylori* agent (amoxicillin, clarithromycin, metronidazole or tetracycline), a cytoprotective agent such as bismuth subsalicylate or sucralfate, or a combination agent such as Helidac or Prevpac.

Pharmaceutical compositions comprising an effective amount of a pharmaceutically acceptable zinc salt alone, or preferably in combination with at least one other zinc salt or an effective amount of a traditional proton pump inhibitor such as such as esomeprazole, lansoprazole, omeprazole, pantoprazole or rabeprazole, an H2 blocker such as cimetidine, famotidine, nizatidine or ranitidine, an anti-*H. pylori* agent, such amoxicillin, clarithromycin (biaxin), metronidazole (flagyl) or tetracycline, a cytoprotective agent such as bismuth subsalicylate or sucralfate, or a combination agent such as Helidac or Prevpac, optionally in combination with a pharmaceutically acceptable carrier, additive or excipient.

Pharmaceutical formulations include those suitable for oral, rectal, nasal, topical (including buccal and sub-lingual), vaginal or parenteral (including intramuscular, subcutaneous and intravenous) administration. Oral compositions or parenteral compositions (especially those for IV administration) are preferred. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired as discussed hereinabove, the present formulations may be adapted to provide sustained release characteristics of the active ingredient(s) in the composition using standard methods well-known in the art. A composition which provides an effective amount of initial dose of zinc salt in the gastric juice at low pH followed by extended release effects of zinc over a longer duration may be preferred.

In the case of combination pharmaceutical compositions, i.e., a composition which comprises at least one water soluble salt in combination with a therapeutic agent (i.e., other than the zinc salt), compositions may be formulated in admixture or they may be compartmentalized in the dosage form. Pharmaceutical formulations may be formulated in admixture by mixing the actives together along with the pharmaceutically acceptable carriers, additives and/or excipients in powder or liquid form and then using directly or presenting the mixture in tablet or capsule form. The compositions may be immediate release, sustained or controlled release or intermediate sustained or controlled release, depending upon the results desired. Formulations may also be presented which compartmentalize the water soluble zinc salt and the therapeutic agent into more than one portion of a tablet or capsule to take advantage of differential solubilities in order to enhance the bioavailability of the zinc salt and/or the additional therapeutic agents, using methods which are readily available in the art to those of ordinary skill.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

In certain preferred embodiments, the present compositions are preferably readily water soluble and mixtures of water-soluble zincs may be used to effect an immediate release/sustained release pharmaceutical profile. This may maximize immediate effect and longer duration effect by simply choose the type of salt and adjusting the ratio of the zinc salt mixture accordingly. Of course, excipients can be chosen to affect the delivery and bioequivalence of the zinc salts used. It is well within the routineer's skill to modify the route of administration and dosage regimen of a particular compound in order to manage the pharmacokinetics of the present compounds for maximum beneficial effect to the patient.

Formulations containing the compounds of the invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, and the like. Preferably, the composition will be about 0.05% to about 75-80% by weight of a zinc salt compound or compounds according to the invention, with the remainder consisting of suitable pharmaceutical additives, carriers and/or excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20%), and optional pharmaceutical additives, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

The present invention also contemplates a route of administration other than an oral route. An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Methods for preparing such dosage forms are known or will be apparent to those skilled in the art; for example, see "Remington's Pharmaceutical Sciences" (17th Ed., Mack Pub. Co., 1985). The person of ordinary skill will take advantage of favorable pharmacokinetic parameters of the pro-drug forms of the present invention, where applicable, in delivering the present compounds to a patient suffering from a viral infection to maximize the intended effect of the compound.

The pharmaceutical compositions according to the invention may also contain other active ingredients such as proton pump inhibitors, $H_2$ blockers, antimicrobial agents, cytoprotective agents or combination agents. In addition, compounds according to the present invention may also contain anti-cancer agents (to treat gastric cancer). Effective amounts or concentrations of each of the active compounds are to be included within the pharmaceutical compositions according to the present invention.

The individual components of such combinations may be administered either sequentially or simultaneously in separate or combined pharmaceutical formulations.

When one or more of the compounds according to the present invention is used in combination with a second therapeutic agent active the dose of each compound may be either the same as or differ from that when the compound is used alone. Appropriate doses will be readily appreciated by those skilled in the art.

The following examples are used to describe the present invention. It is understood that they are merely exemplary and are understood not to limit the breadth of the invention in any way.

EXAMPLES

The stomach produces acid to help break down food, making it easier to digest. In some cases, stomach acid can actually irritate the lining of the stomach and the duodenum (top end of the small intestine). Sometimes the acid "refluxes" upwards and irritates the lining of the esophagus. Irritation of the lining of the stomach or the esophagus causes acid indigestion (heartburn) and sometimes causes ulcers or bleeding.

We show in this particular application that $ZnCl_2$ has a potent inhibitory effect on gastric acid secretion at the cellular level by abolishing the activity of the gastric $H^+,K^+$-ATPase in rat and human gastric glands. We also demonstrate that addition of micromole concentrations of $ZnCl_2$ can effectively prevent histamine dependent acid secretion in whole rat stomachs and through a $ZnCl_2$ enriched diet.

Material and Methods

Animals.

Sprague-Dawley rats 150-250 g (Charles River Laboratory)) were housed in climate- and humidity-controlled, light-cycled rooms, fed standard chow with free access to water, and handled according to the humane practices of animal care established by the Yale Animal Care. Prior to experiments, animals were fasted for 18-24 hours with free access to water.

Isolation of Rat and Human Gastric Glands.

Following removal of the stomach, the stomach was opened longitudinally and the corpus and antrum isolated and sliced into 0.5 cm square sections, and washed with cold Ringer solution to remove residual food particles. The tissues were transferred to the stage of a dissecting microscope. Individual glands were isolated using a hand-dissection technique as described previously[36]. Following isolation, individual isolated glands were allowed to adhere to cover slips that had been pre-coated with Cell-Tak (Collaborative Research, Bedford, Mass.) and were transferred to the stage of an inverted microscope.

The human tissue was transferred from the OR in a HEPES-buffered Ringer solution. The tissue was stored on ice and immediately the isolated glands were dissected as described above.

Digital Imaging for Intracellular pH.

Isolated gastric glands were incubated in a HEPES-buffered Ringer's solution containing either 10 μmol of the pH-sensitive dye BCECF-AM (2',7')-bis-(2-carboxyethyl)-5-(and -6)-carboxy-fluorescin, aceto-methyl ester (Molecular Probes, Eugene, Oreg.) for 10 minutes as described previously[37-39]. Following dye-loading the chamber was flushed with a HEPES solution to remove all non-de-esterified dye. The perfusion chamber was mounted on the stage of an inverted microscope (Olympus IX50), which was used in the epifluorescence mode with a 40× objective. BCECF was successively excited at 440 nm and 490 nm from a monochromator light source, and the resultant fluorescent signal was monitored at 535 nm using an intensified charge-coupled device camera. Individual regions of interest were outlined and simultaneously monitored every 15 sec. during the course of the experiment. A minimum of 8 cells or regions was selected per gland.

Proton extrusion by individual parietal cells was monitored by observing recovery of $pH_i$ after acid loading the cells with $Na^+$ free HEPES solution containing 20 mM $NH_4Cl$. Parietal cells were subsequently superfused with $Na^+$ free HEPES, which abolished all $Na^+/H^+$ Exchanger (NHE) activity, trapping $H^+$ within the cytosol and initiating an immediate drop in pHi. Under these conditions, the only potential $H^+$ extrusion pathway is via the $H^+,K^+$-ATPase activation.

The intensity ratio data (490/440) were converted to pH values using the high $K^+$/nigericin calibration technique[40]. Intracellular pH recovery rates were calculated from the same initial starting pH to eliminate the potential variation in the individual intracellular buffering power of the cells under the different experimental conditions. All data including the individual images for all wavelengths were recorded to the hard disk which allowed us to return to the individual images after the experiment for further analysis. The recovery rates are expressed as the ΔpH/min, and were calculated over the pH range of 6.5-6.8. All chemicals were obtained from Sigma and Molecular Probes. All data were summarized as means±SE and were analysed by grouping measurements at baseline values.

Whole Stomach pH Measurements.

Before the experiments animals were fasted for 24 h to reduce basal acid secretion to a consistent minimum. Animals were killed with an overdose of isoflurane and an abdominal incision was made. The stomach was ligated at the duodenal and esophageal junction and excised. Then 1 ml of non buffered, isotonic saline (140 mM) was infused into the lumen of the stomach. This volume did not distend the stomach, thus avoiding potential stimulation of acid secretion by stretch. The stomachs were then placed in either oxygenated HEPES-buffered Ringer solution or in the same solution containing 100 μM histamine alone or additionally 300 μM $ZnCl_2$ (pH 7.4) and maintained at 37° C. After 1 hour the stomach contents were aspirated and the pH was recorded.

Oral Zinc Supplementation in Rats.

These studies were designed to modulate acid secretion by increasing dietary zinc. In these studies we used an oral $ZnCl_2$ solution (zinc chloride in tap water). The animals had free access to food and the zinc containing water for the duration of the study. 150 mg/kg/d or 0.5 mg/kg/d $ZnCl_2$ was added to the drinking water for 5 days. Animals had free access to water prior to the experiment and were fed with standard chow until 24 hours before the experiment, at which point they had free access to $ZnCl_2$ containing water only. After the 5 days exposure period and the 24 hour fast, the animals were sacrificed and a total gastrectomy was performed on the animals. Individual gastric glands were isolated with the hand dissection technique described above.

Results

Histamine Induced Acid Secretion in Human and Rat is Inhibited by $ZnCl_2$.

In the first series $pH_i$ measurements of single parietal cells within freshly isolated gastric glands were used to measure $H^+,K^+$-ATPase activity. The activity of the proton pump was calculated from the rate of alkalinization of $pH_i$ ($ΔpH_i$/min) after acidification using the NH4Cl prepulse technique in the absence of sodium and bicarbonate. H$^+$ extrusion under these conditions depends on the activity of the H$^+$,K$^+$-ATPase, as previously shown[41]. In the absence of any stimulation, only a low rate of pHi recovery was observed (0.011±0.002 units/min, n=32 cells from 3 glands from 3 animals; FIG. 1 E). After exposure of the rat gastric glands to histamine (100 µM), the alkalinization rate increased to 0.051±0.004 pH units/min (n=60 cells from 15 glands from 8 animals; FIG. 1 A). Adding 300 µM ZnCl$_2$ to the superfusion bath in the presence of histamine (100 µM) prevented the stimulatory effect of histamine on the Na$^+$-independent recovery rate (0.0012±0.004 pH units/min) and reduced it to the same level as seen in the control glands not exposed to histamine (n=60 cells from 6 glands from 4 animals); FIG. 1 B). Human gastric glands showed also a robust proton efflux under histamine stimulation. This effect was abolished by ZnCl$_2$ (FIG. 1C, D); (n=26 cells, 3 glands). Thus the freshly isolated rat and human gastric glands showed H$^+$,K$^+$-ATPase activity that could be stimulated by histamine and inhibited by ZnCl$_2$.

ZnCl$_2$ Inhibits Rat Acid Secretion in a Dose Dependent Manner.

Figure 2:
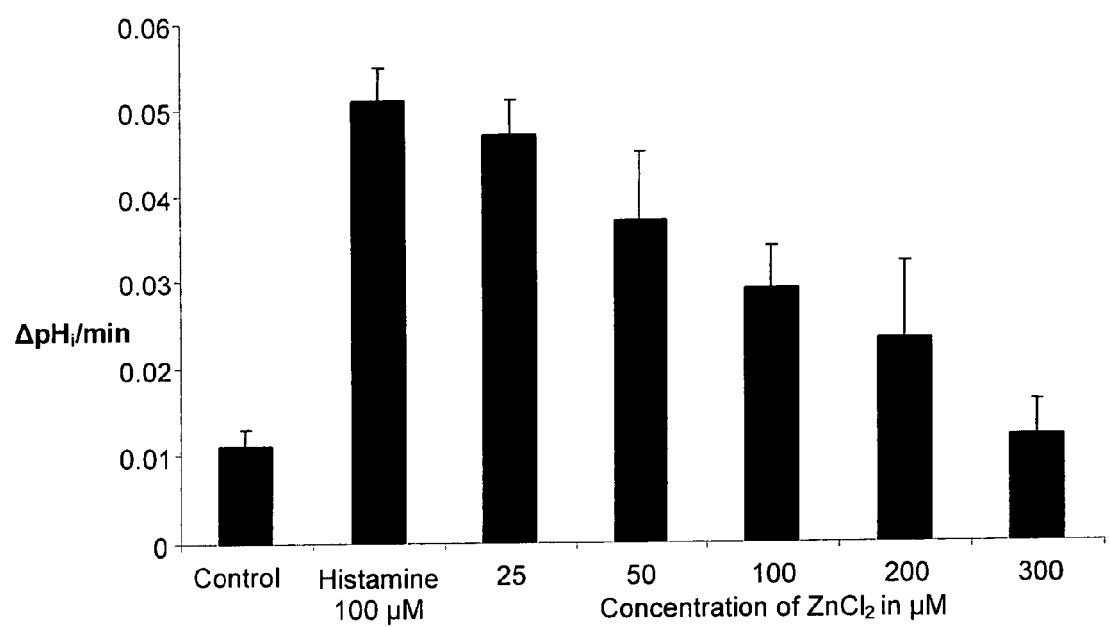
FIG. 2 shows that $ZnCl_2$ inhibits acid secretion in a dose dependent manner. $ZnCl_2$ concentration dependence of $H^+/K^+$-ATPase activity (intracellular alkalinization expressed as ΔpH/min) in the presence of 100 μmol histamine in comparison to basal and histamine induced acid secretion. (n=40 cells, 3-4 glands, 3-4 animals for each $ZnCl_2$ concentration).

ZnCl$_2$ inhibited H$^+$ extrusion in a dose dependent manner (FIG. 2). In this protocol acid secretion was stimulated by histamine and expressed as ΔpH$_i$/min. Therefore rat gastric glands were incubated with 100 µM histamine (15 min) and histamine was present throughout the entire experiment. To investigate the inhibitory potency of ZnCl$_2$ we used different concentrations (25 µM-300 µM). ZnCl$_2$ was present during the entire experiment, including the histamine incubation period of 15 min. 300 µM ZnCl$_2$ showed a 98% inhibition of proton extrusion compared to the Histamine induced rate and the control.

Fast Onset and Reversible Inhibition of Gastric Acid Secretion by ZnCl$_2$.

Figure 3:
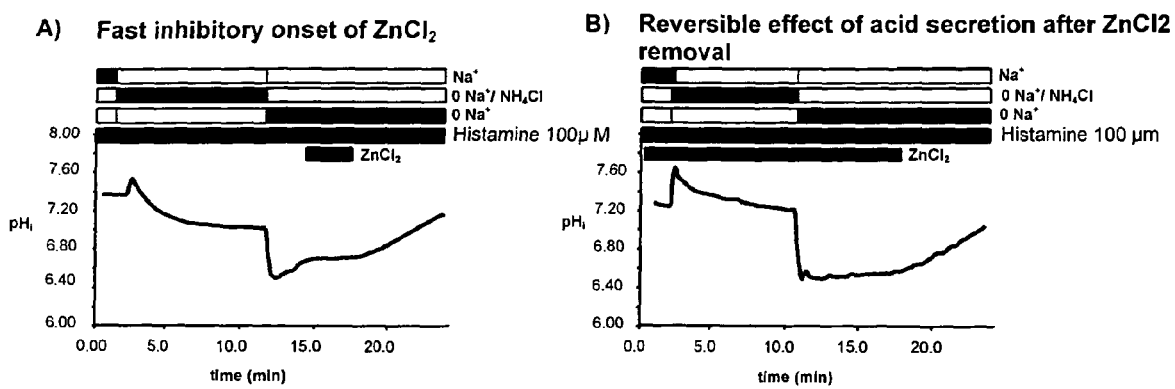
FIG. 3 show the fast onset inhibitory effect and reversibility with $ZnCl_2$. (A) original tracing shows the fast inhibitory effect of $ZnCl_2$ on histamine induced acid secretion. Histamine (100 μM) was added through the whole experiment. When the intracellular alkalinization (protonefflux) was observed, $ZnCl_2$ (300 μM) was added to the superfusion bath. The acid secretion was abolished after a few seconds (flat middle part). After the removal of $ZnCl_2$ out of the perfusion bath the drug was washed out and the increase of the intracellular pH continued. (B) Original tracing shows the reversibility after the cells where incubated and superfused over 20 min with $ZnCl_2$ (300 μM) and histamine (100 μM). After removal of $ZnCl_2$ out of the superfusion bath the intracellular alkalinization (proton extrusion) occur.

There are irreversible (i.e. omeprazole) and reversible (P-CAB's) acid blockers available[42]. We investigate the reversibility of the inhibitory effect of ZnCl$_2$ in our in vitro setting. Thus we stimulated acid secretion with histamine (100 µM) during the entire experiment. When the intracellular alkalinization (acid secretion) was observed, ZnCl$_2$ (300 µM) was added to the superfusion bath. The acid secretion was abolished after a few seconds (FIG. 3 A). After the removal of ZnCl$_2$ in the same experiment acid secretion returns to normal levels. We were also able to demonstrate reversibility following incubation and superfusion of parietal cells over 20 min with ZnCl$_2$ (300 µM) and histamine (100 µM). After removal of ZnCl$_2$ from the superfusion bath the intracellular alkalinization (proton extrusion) proceeded at normal uninhibited rate (FIG. 3 B).

Oral Zinc Supplementation Reduces Basal Rat Gastric Acid Secretion.

Figure 4:
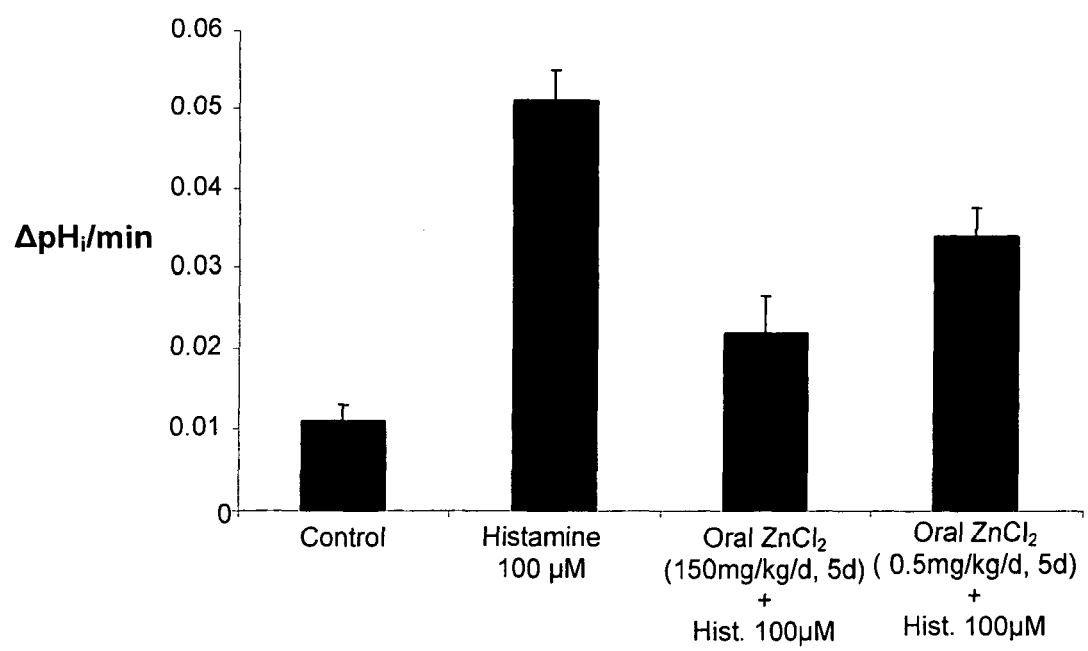
FIG. 4 shows acid secretion after oral $ZnCl_2$ application. 300 μmol $ZnCl_2$ was added to the drinking water. Animals ate and drank as much as control animals. Prior the experiment they were fasted for 12-18 hours. The histamine induced acid secretion was measured as described before. The cells of the $ZnCl_2$ treated animals showed a lower rate of proton efflux. 150 mg/kg/d: 0.022±0.0045; (n=60 cells, 10 glands, 3 animals), 0.05 mg/kg/d: 0.034±0.0036; (n=60 cells, 6 glands, 4 animals).

These studies were designed to modulate acid secretion by increasing dietary zinc. 150 mg/kg/d or 0.5 mg/kg/d ZnCl$_2$ were added to the drinking water for 5 days. The H$^+$ extrusion rate was measured with BCECF as described before. Histamine stimulated parietal cells showed a robust recovery rate (proton extrusion) of 0.051±0.004 (n=120 cells from 15 glands from 8 animals). FIG. 4 shows that the ZnCl$_2$ (150 mg/kg/d or 0.5 mg/kg/d) in the drinking water decreased the histamine induced acid secretion significantly in comparison to the control group with histamine alone. 150 mg/kg/d: 0.022±0.0045; (n=60 cells from 10 glands from 3 animals), 0.05 mg/kg/d: 0.034±0.0036; (n=60 cells from 6 glands from 4 animals).

ZnCl$_2$ Decreased Gastric Acid Production Ex Vivo.

Figure 5:
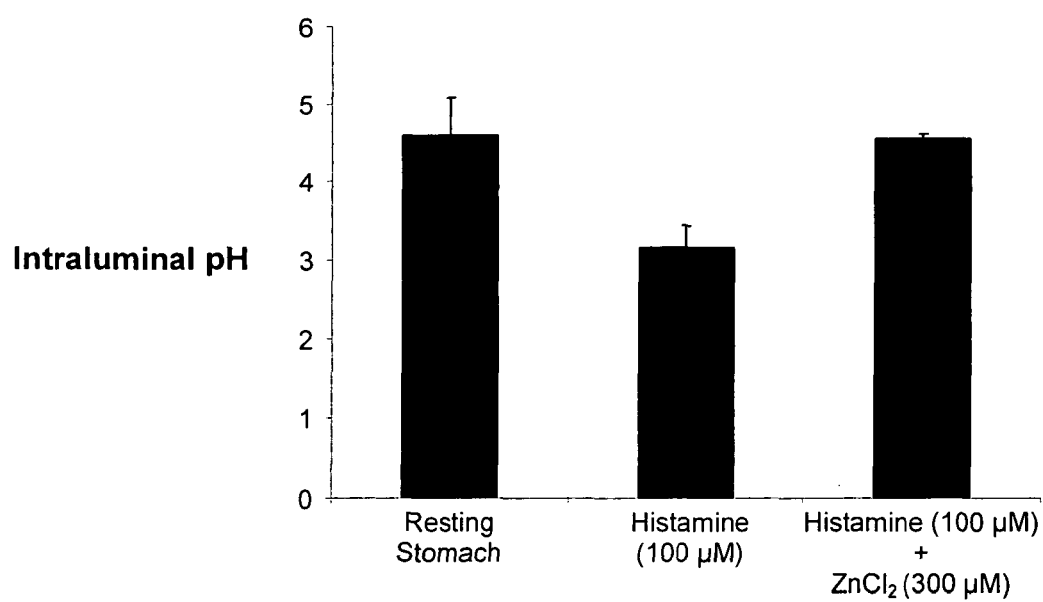
FIG. 5 shows that $ZnCl_2$ inhibits gastric acid secretion in freshly isolated rat whole stomach preparation. Ex vivo rat whole stomach preparations were incubated in HEPES-buffered Ringer solution (control: n=9), HEPES-buffered Ringer solution plus 100 μM histamine (n=8), or HEPES-buffered Ringer solution plus 100 μmol histamine and 300 μmol $ZnCl_2$ (n=8). Stomach preparations incubated with histamine and ZnCl2 had a higher pH than those in HEPES-buffered Ringer solution and histamine and their pH was similar to the pH of the control stomach.

To determine whether ZnCl$_2$ could inhibit gastric acid secretion in the whole organ, we examined luminal pH in freshly isolated rat stomachs after incubation in HEPES or in the same solution the presence of 100 µM histamine or both, 100 µM histamine and 300 µM ZnCl$_2$. As illustrated in FIG. 5, in the presence of histamine mean luminal pH was lower than in control stomach preparations incubated in HEPES alone (3.15±0.27 vs. 4.59±0.48, n=9 for each, P<0.005). In the presence of histamine and ZnCl$_2$ the luminal pH was nearly as high as in the control group without stimulation although this findings were not significant (4.54±0.065 vs. 4.59±0.48, n=8 each group, P>0.005).

Different Zinc Salts Shows Different Efficacy in Raising Intraluminal pH.

Figure 6:
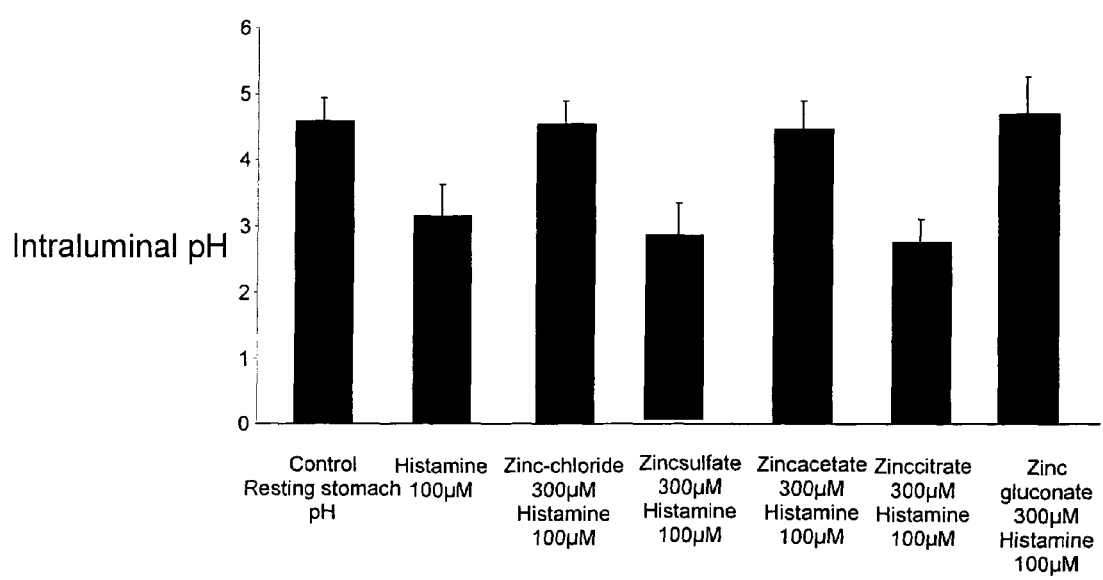
FIG. 6 shows measurements of whole stomach intraluminal pH using a number of zinc salts according to the present invention. Isolated whole stomach preparations from rats were cannulated at the esophageal and duodenal junction and perfused in vitro with 37° C. pH 7.4 Ringers solution. The blood perfusate was then exposed to 100 μM Histamine to induce acid secretion. The lumen of the stomach was infused with 0.5 cc of non-buffered isotonic saline. In some studies one of the following zinc salts was added to the lumen perfusate at a final concentration of 300 μM (zinc chloride, zinc sulfate, zinc acetate, zinc citrate). The data are the sum of 5 separate stomachs from 5 separate animals for each of the columns. Data are the mean of all studies with the standard error of the mean displayed.

Measurements of whole stomach intraluminal pH using a number of zinc salts according to the present invention were made to assess effect of salt and concentration on intraluminal pH. Isolated whole stomach preparations from rats were cannulated at the esophageal and duodenal junction and perfused in vitro with 37° C. pH 7.4 Ringers solution. The blood perfusate was then exposed to 100 µM Histamine to induce acid secretion. The lumen of the stomach was infused with 0.5 cc of non-buffered isotonic saline. In some studies one of the following zinc salts was added to the lumen perfusate at a final concentration of 300 µM (zinc chloride, zinc sulfate, zinc acetate, zinc citrate). The data are the sum of 5 separate stomachs from 5 separate animals for each of the columns. Data are the mean of all studies with the standard error of the mean displayed. Those results appear in attached FIG. 6.

Discussion

In this study, we examined the dose dependent inhibition of gastric acid secretion by ZnCl$_2$ in human and rat gastric glands. Furthermore we tried to evaluate the onset of effect of ZnCl$_2$ and used whole stomach preparation as well as oral Zinc supplementation to investigate the effect on gastric acid secretion.

Acid secretion was induced by the classically known secretagogue histamine, which led to a robust proton extrusion via the H$^+$,K$^+$-ATPase in comparison to basal acid secretion in the resting, unstimulated gland (FIG. 1e). In subsequent studies we examined the inhibitory effects of ZnCl$_2$ on secretagogue sensitive gastric acid secretion. We confirmed the inhibitory potency of ZnCl$_2$ (300 µM) on histamine induced acid secretion. ZnCl$_2$ inhibits acid secretion in the single gastric gland in a dose dependent manner. ZnCl$_2$ abolished proton extrusion to a level comparable to that of the control experiments in both, human and rat gastric glands (FIG. 1). This dose would be equivalent to 40 mg supplementation per day in humans. The daily recommended amount of Zinc intake is 11 mg. In the literature the amount considered to be toxic is 10 times higher. Therefore 40 mg of ZnCl$_2$ as an oral acid blocker would be significantly lower than reported toxic doses. In addition a similar amount of ZnCl$_2$ also prevented acid secretion in ex vivo whole stomach preparations (FIG. 5). In these experiments ZnCl$_2$ was applied to the luminal side of the stomach and it can thus be concluded that the metal ion is working directly on the H$^+$,K$^+$-ATPase of the parietal cell or enters the cell to modulate the signalling pathway of acid secretion. It remains unclear how ZnCl$_2$ enters the cell. Previous studies described Zinc entry into the cell through voltage dependent Ca$^{2+}$-channels and/or the HCO$_3$/Cl$^-$ exchanger on the basolateral membrane. Orally applied ZnCl$_2$ confirmed our previous results. Proton extrusion by ZnCl$_2$ treated rats was significant lower than acid secretion by our control group (FIG. 4). The control refers to histamine stimulated. In the figure, zinc treated glands are still higher than the control (non-histamine treated) alone.

As mentioned in the introduction proton pump inhibitors have a delayed onset of acute action and the full inhibitory effect is slow requiring several dose cycles. For example omeprazole reaches only 30% inhibition of acid secretion on the first day of treatment[43]. Our study characterizes the rapid onset of action $ZnCl_2$ as well as its reversibility. Faster onset of effect and increased duration of action would offer improvement for patients with GERD and other acid related disorders. In fact as shown in FIG. 5a we were able to inhibit histamine induced acid secretion during maximal proton extrusion by addition of 300 μM $ZnCl_2$. On the other hand histamine induced acid secretion continued after removal of $ZnCl_2$ from the superfusion bath demonstrating the reversible nature of $ZnCl_2$ (FIG. 3 b).

In summary our findings indicate that $ZnCl_2$ offer a more rapid and prolonged inhibition of gastric acid secretion. It is a reversible and fast acting inhibitor of acid secretion in single rat and human gastric glands and also in whole stomach preparations.

Such treatment may provide significant benefit to patients with GERD. Future studies investigating the exact mechanism by which $ZnCl_2$ inhibits acid secretion are necessary and will help define its future place in the treatment of acid related diseases in the clinical setting.

Fundic Region

In the following examples, it is shown that the fundic region of the stomach and the fundic glands contain functional acid secretory proteins. Furthermore, it is shown that the fundic glands have a sodium and potassium independent protein the proton ATPase commonly referred to as the Vacuolar $H^+$-ATPase. The evidence consists of immunofluorescence data using a antibody directed against the a Subunit of the $H^+$-ATPase and functional data (FIGS. 7-10) in which the extrusion rate of protons from these cells in the absence of Na and K is measured. Further there is evidence that this process is amplified in the presence of histamine a compound that was thought to only influence the gastric $H^+,K^+$-ATPase found in the parietal cells in the body of the stomach. This activity is demonstrated in both the rat model and in humans in gastric resections taken from patients undergoing gastric reduction surgery.

Materials and Methods

Animals and Chemicals

Male Sprague Dawley rats weighing 200-300 g were housed in climate and humidity controlled, light cycled rooms and fed standard chow with free access to water. Prior to experiments, animals were fasted while allowing free access to water for 18-24 hours to reduce basal acid secretion. Following isoflurane anesthesia the animals were sacrificed, an abdominal incision was made exposing the stomach. After isolating the esophagus and duodenal junctures a total gastrectomy was performed with 1-2 cm of esophagus remaining attached to the gastrectomy. We included the esophageal juncture to have a common landmark for all fundic isolations. While holding the esophagus with forceps approximately 3 mm of fundus was removed with 5 mm of the intact esophagus.

Fundic Gland Isolation

The removed fundic tissue was placed in ice cold HEPES-buffered Ringer-solution (pH adjusted to 7.4 at 4° C.) and transferred to the stage of a dissection microscope. The fundic glands were visualized under the microscope at 50× magnification. Glands adjacent to the esophageal junction were hand dissected. Following isolation, individual glands were adhered to cover slips that had been pretreated with the biological adhesive Cell-Tak (Cell-Tak™ cell adhesive, BD Biosciences; Bedford, Mass.)

Immunohistochemistry/Immunofluorescence

Male Wistar rats (200-250 g) were anesthetized with pentobarbital i.p. and perfused through the left ventricle with PBS followed by paraformaldehyde-lysine-periodate (PLP) fixative as previously described[19a]. Stomachs were removed, cleaned from food residues, and fixed overnight at 4° C. by immersion in PLP. Stomachs were washed three times with PBS and sections were cut at a thickness of 5 μm after cryoprotection with 2.3 M in PBS for at least 12 h. Immunostaining was carried out as described previously[20a]. Sections were incubated with 1% SDS for 5 min., washed 3 times with PBS and incubated with PBS containing 1% bovine serum albumin for 15 min prior to the primary antibody. The primary antibodies (mouse monoclonal anti human β gastric $H^+,K^+$-ATPase (Affinity Bioreagents, CA, USA) diluted 1:50 in PBS and applied overnight at 4° C. Sections were then washed twice for 5 min with high NaCl PBS (PBS+2.7% NaCl), once with PBS, and incubated with the secondary antibody (donkey anti-rabbit Alexa 546, Molecular Probes, Oregon) at a dilution of 1:1000 for 1 h at room temperature. Sections were washed twice with high NaCl PBS and once with PBS before mounting with VectaMount (Vector Laboratories, Burlingame, Calif.). The specimens were viewed with a Nikon E-800 microscope.

ImmunoGold Labeling

Rats were anaesthetized using 5 ml of a 10% sodium pentobarbital given i.p. Fixation was done through a left ventricle cardiac perfusion using PBS and then PLP. The stomach was removed and fixed in PLP for 4 hours and then transferred to holding buffer overnight. Frozen and Epon sections of the gastro esophageal junction were made and slices were taken for gold labeling and electron microscopy.

Hematoxylin and Eosin Staining

Rats were anaesthetized using 5 ml of a 10% sodium pentobarbital given i.p. Fixation was done through a left ventricle cardiac perfusion using PBS to flush the animal and then Karnovsky Fixative for 2 hours and then in holding buffer overnight. A section of the gastro esophageal junction were made and slices taken for Electron Microscopy morphology of the $H^+,K^+$-ATPase protein and Hematoxylin/Eosin staining of the glands at the gastro esophageal junction.

Measurements of Intracellular pH ($pH_i$) Measurements of Isolated Fundic Glands Using the same protocol that we developed for isolated corpus gland perfusion[20a, 21a] individual fundic glands were loaded with a 1004 concentration of the pH sensitive dye (BCECF, (2'7-bis(2-carbocyethal)-5-(and 6)-carboxyflurorescein-acetomethylester; Molecular Probes, OR USA)) for 15 minutes. Following the loading period, the perfusion chamber was mounted on the stage of an inverted microscope (Olympus IX50) attached to a digital imaging system (Universal Imaging Corp; Dowingtown, Pa.), and perfused with HEPES buffered Ringer-solution for 5 min at 37 C.° to remove any unesterified dye. Measurements were performed in the epifluorescence mode with 60×/0.80 and 40×/0.90 objectives. BCECF was successively excited at 440±10 nm and 490±10 nm, the resultant intracellular fluorescent signal was monitored at 535 nm using an intensified charge-coupled device camera. Data points were acquired every 15 s. The resulting 490/440 intensity ratio data were converted to intracellular pH ($pH_i$) values using the high $K^+$/Nigericin calibration technique[22as, 22as]. Acid extrusion was monitored in the absence of bicarbonate. The rate of intracellular alkalinization was measured after using the $NH_4Cl$-prepulse technique[22a, 23a], which resulted in a reproducible and sustained intracellular acidification. Intracellular pH recovery rates ($H^+$, $K^+$-ATPase activity) were measured in $Na^+$ free HEPES solutions containing: 1) 100 μM histamine 2) 100 μM pentagastrin. 3) 100 μM acetylcholine 4) 100 μM histamine+ omeprazole at 100 μM and 200 μM concentrations.

Intracellular pH recovery rates were calculated from the same initial starting pH to eliminate the potential variation in the individual intracellular buffering power of the cells under the different experimental conditions. All data including the individual images for all wavelengths were recorded to the hard disk which allowed us to return to the individual images after the experiment for further analysis. The recovery rates are expressed as the $\Delta pH_i/min$, and were calculated over the pH range of 6.5-6.9.

Activation of acid secretion via histamine, acetylcholine or pentagastrin was induced by preincubation of the glands for 15 min before the experiment combined with BCECF (100 μM) loading. All data are summarized as mean±S.E. Significance was determined using the one-way ANOVA test with p<0.05 considered to be statistically significant. All chemicals used were obtained from Sigma and Molecular Probes.

Results

Immunohistochemical Localization of the $H^+$, $K^+$-ATPase

Immunohistochemistry using specific antibodies directed against highly conserved epitopes within either the α or β subunits of the gastric $H^+$, $K^+$-ATPase identified specific staining for both subunits in the fundic glands (FIG. 7 A).

Electron Microscopy

After obtaining Epon sections of fasted rat gastro esophageal junction Electron Microscopy was done on the gastric glands that came right after this junction and those we named F1 and used in all of our experiments. FIG. 7 B, C shows the gold tag localization to the $H^+$, $K^+$-ATPase in the parietal cell from the Fundic gland. We noticed a higher density of staining on the apical pole of the cell in the secretory or vacuolar canaliculi. This may correlate with the fundic regions high basal proton extrusion rates in comparison to the corpus due to the fact that the protein is always at the membrane in the fundic gland whereas in the corpus the receptor is inside the secretory canaliculus until stimulation.

H2 Receptor Staining

H2 receptor staining was done on both the fundus and corpus to examine the presence and density of the receptor in both the areas of the stomach. We found clear basolateral staining in the corpus glands and could not detect staining in the fundic glands. These results correlate with the lack of effect by histamine in stimulating fundic acid secretion. It was clearly seen that the H2 receptor is absent in the glands of the fundus and present in the corpus (data not shown)

Secretagogue Induced Acid Secretion

Intracellular pH was measured using the pH sensitive dye BCECF and monitored continuously using a real time fluorescence imaging system to identify changes in intracellular pH. Rates of proton efflux were calculated as $\Delta pH_i/min$ using a technique that was developed in our laboratory for corpus glands[21a-25a]. We measured the change in rate of efflux in the presence and absence of secretagogues.

Histamine Effect on Fundic and Corpus $H^+$, $K^+$-ATPase

We incubated individual glands with 100 μM histamine for 20 minutes. Histamine was present during the whole superfusion protocol. In the corpus gland we measured a histamine stimulated proton extrusion rate of 0.056±0.008 $\Delta pH_i/min$ whereas the basal acid secretion without any secretagogues was 0.011±0.002 $\Delta pH_i/min$ (FIG. 8C, D). In comparison to the corpus the fundus showed even under basal conditions a high proton extrusion rate (0.039±0.009 $\Delta pH_i/min$). This is similar to the histamine induced acid secretion (0.040±0.0079 $\Delta pH_i/min$, FIG. 8 A, B) This data shows that there is no effect of histamine on F1 zone glands in comparison to controls.

Acetylcholine and Fundic Acid Secretion

Figure 9:
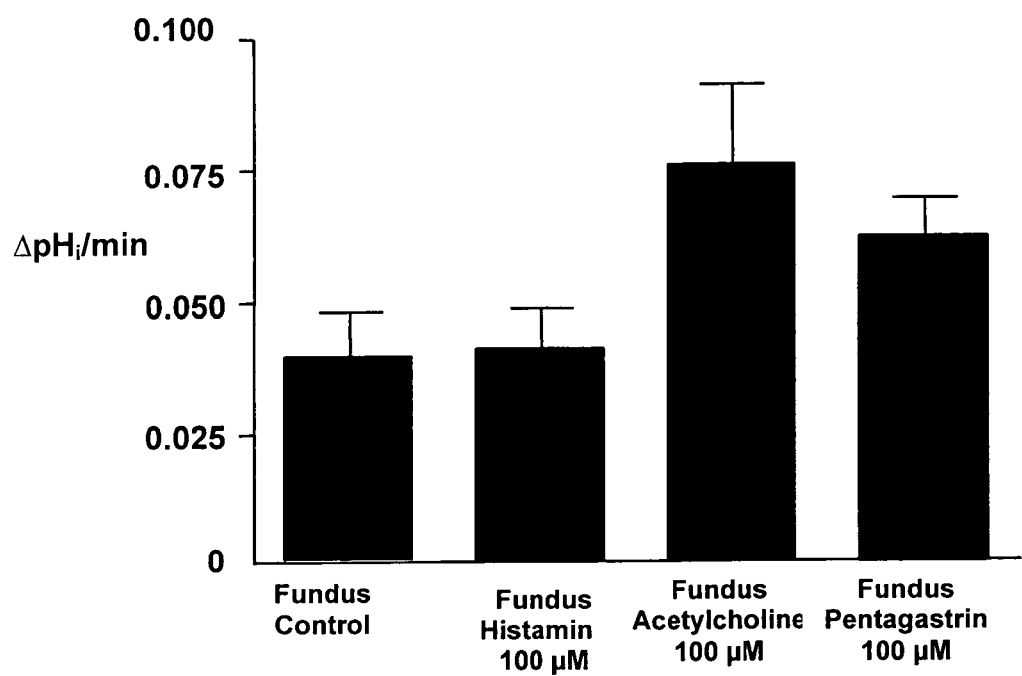
FIG. 9 shows a secretagogue series of F1 glands. F1 gland under basal condition with no stimulation shows alkalinization rates of 0.039 $\Delta pH_i$/min±0.009 (n=52 cells/8 glands/5 animals). In the presence of 100 μM histamine recovery rates were 0.042±0.007 $\Delta pH_i$/min (n=64 cells/8 glands/6 animals). In the presence of 100 μM acetylcholine F1 glands alkalinized at a rate of 0.075±0.0015 $\Delta pH_i$/min (n=86 cells/10 glands/6 animals). In the presence of 100 μM pentagastrin F1 glands show alkalinization rates of 0.062±0.007 $\Delta pH_i$/min (n=49 cells/6 glands/5 animals).

In the next series we investigated the functional properties of fundic glands according to the neuronal stimulation via ACH. In contrast to histamine there was a noticeable change in proton extrusion rates after stimulation. Although the controls were still actively pumping out protons the glands that were stimulated with 100 μM of acetylcholine for 20 minutes during the dye loading and throughout the perfusion. We determined that acetylcholine caused an increase in the rate of alkalinization (0.075±0.0015 $\Delta pH_i/min$ vs. controls 0.039±0.009 $\Delta pH_i/min$) showing a direct effect of acetylcholine on fundic acid extrusion (FIG. 9).

Pentagastrin Effect on the F1 Zone

To determine if gastrin could also activate the fundic $H^+$, $K^+$-ATPase we conducted studies using pentagastrin, a synthetic peptide containing the entire five terminal amino acids of gastrin, which is know to cause robust acid secretion in corpus glands. At a dose of 100 μM pentagastrin we observed alkalinization rates that were 0.062±0.007 $\Delta pH_i/min$ which was similar to acetylcholine in terms of enhancing the rate of proton extrusion from fundic cells (FIG. 9).

Inhibitors of Gastric Acid Secretion

In the next series of studies we tried to determine if the fundic glands had similar $H^+$, $K^+$-ATPase inhibitor profiles as observed in the corpus. We chose the well characterized inhibitor of the gastric $H^+$, $K^+$-ATPase omeprazole and the P-CAB (potassium competitive acid blocker) AZD0865.[26,27]

Omeprazole Effect on the F1 Zone and Corpus

As shown in FIG. 10 A, omeprazole did not inhibit acid secretion using the same concentration that completely inhibited secretagogue induced acid secretion in the corpus (FIG. 10 B). At even a higher dose than what normally inhibits acid secretion in the corpus the fundus continued to extrude protons. The fundic glands were preincubated with 200 μM omeprazole and 100 μM histamine and then perfused with omeprazole and histamine throughout the entire experiment. Alkalinization rates were 0.045±0.002 $\Delta pH_i/min$ compared to only histamine stimulated controls at a rate of 0.042±0.007 $\Delta pH_i/min$. In contrast acid secretion in the corpus glands was abolished by 200 μmol omeprazole (0.014±0.002 $\Delta pHi/min.$), (FIG. 10 B).

AZD0865 Effect on the F1 Zone in Comparison to the Corpus:

Also shown in FIG. 10 (C, D), P-CAB AZD0865 effectively inhibits acid secretion in the corpus at a 10 μM concentration; however at that same concentration the F1 zone still has potassium dependant recovery. In the fundus the intracellular pH increased at a rate of 0.031±0.006 $\Delta pH_i/min$. In the Corpus at the same concentration of 10 μM the recovery rate was 0.021±0.008 $\Delta pH_i/min$.

Table 1

Composition of Solutions Used for Intracellular pH Measurements in Single Rat Gastric Glands.

All concentrations are given in Mm. NMDG is N-Methyl-D-Glucosamine, all solutions were titrated to pH 7.4 at 37° C. using either NaOH or KOH. NMDG was titrated with HCL.

TABLE 1

| | Solution 1: Standard HEPES | Solution 2: Na$^+$ - free HEPES | Solution 3: Na$^+$ - free HEPES + NH4Cl | Solution 4: High K$^+$ calibration |
|---|---|---|---|---|
| NaCl | 125 | — | — | — |
| NMDG | — | 125 | 125 | 125 |
| NH$_4$Cl | — | — | 20 | — |
| KCl | 3 | 3 | 3 | 105 |
| MgSO$_4$ | 1.2 | 1.2 | 1.2 | 1.2 |

TABLE 1-continued

|  | Solution 1: Standard HEPES | Solution 2: Na$^+$ - free HEPES | Solution 3: Na$^+$ - free HEPES + NH4Cl | Solution 4: High K$^+$ calibration |
|---|---|---|---|---|
| CaCl$_2$ | 1 | 1 | 1 | 1 |
| Glucose | 5 | 5 | 5 | — |
| HEPES | 32.2 | 32.2 | 32.2 | 32.2 |
| pH | 7.4 | 7.4 | 7.4 | 7.0 |

Discussion

In this study we have provided evidence that the fundic region of the stomach contains glands that are capable of secreting acid via the gastric H$^+$, K$^+$-ATPase. In our study we have for the first time characterized the acid secretory properties of the fundus. We provide morphological, immunohistochemical and functional evidence for H$^+$, K$^+$-ATPase protein activity in the fundus In our morphological studies we first had to delineate where the fundus began and ended. As it is understood that this region begins at the gastro esophageal junction we decided to take glands from this junction point until the initiation of the greater curve of the fundus. We took tissue sections from what we called the F1 zone starting from the gastro esophageal junction and continued 2 mm distally. We found these glands to be quite different in shape and also in parietal cell like density. To confirm that parietal cells in F1 contain H$^+$, K$^+$-ATPase we stained for the α and β subunit (FIG. 7 shows the staining for the α subunit).

During our investigation of secretagogue induced fundic acid secretion we were able to demonstrate that histamine is not the most potent stimulator of acid secretion in the fundus as it is in the corpus. In fact, very little difference was seen in glands that were not stimulated compared to those stimulated with histamine (FIGS. 8 and 9). This result was confirmed by a lack of staining for the H2 receptor in the fundus (data not shown). Acetylcholine was the most robust of the three secretagogues in the fundus, which may relate to the close proximity of the vagal nerve to the fundic region. As this section of the stomach stretches when food is present, there is vagal stimulation[28a-30a] with associated acetylcholine secretion. This finding is especially important when considering clinical problems in obese patients who have gastro esophageal reflux disease (GERD). This can be correlated to the benefits patients with sever ulcer disease gain when undergoing a vagotomy after not gaining relief from medical management[31a-33a].

Another interesting finding is the lack of inhibition by omeprazole on fundic acid secretion although they are immunoreactive with antibodies for the gastric H$^+$, K$^+$-ATPase. We were unable to inhibit basal or secretagogue (histamine) induced fundic acid secretion with the proton pump inhibitor omeprazole (FIG. 10 A) at doses that were double that which effectively eliminated all acid secretion in the corpus (FIG. 10 B). These findings are in direct contrast to our data (FIG. 8 C, D)[20a, 21a, 24a, 25a] and others findings in glands from the corpus[34a-38a] This finding has an interesting clinical correlate in that there is an increasing number of patients suffering from GERD that are not effectively treated with PPI's.[39a] One possible explanation for the lack of omeprazole sensitivity could be that as omeprazole needs to be acid activated, a lack of a canaliculi like space would prevent the concentration of acid and potentially prevent the acid activation of the drug. As shown in FIG. 7 B, C using immunogold tag labeling we see that there is indeed a secretory space and that the pumps appear to line the apical surface of this space. With previous theories of acid secretion came the many dictums for surgical and medical modalities of treatment which focused on the corpus. Of interest is the recent incidence of GERD like symptoms in gastric bypass patients who following the procedure are left only with a small part of the fundus, and little to no functional corpus. In those symptomatic patients there has been little to no success using classical PPI's[40a] which now can be possibly be explained by our recent findings. Our findings demonstrate that the fundic region of the stomach is much more than a holding area and in fact can secrete acid in response to secretagogue stimulation, furthermore the H$^+$, K$^+$-ATPase found in this segment appears insensitive to omeprazole. These results can lead to important new targets for patients that are PPI resistant or have recurrent reflux symptoms in the presence of PPI therapy.

Results:

Fundic glands showed a distinct morphology compared to corpus glands (elongated and lacking typical bulging parietal cells). Immunofluorescence (α and β subunit of the H$^+$, K$^+$-ATPase) and immunogold labeling (β subunit) were both positive in the fundic region. Fundic gland proton extrusion rates were stimulated by gastrin and acetylcholine but were not influenced by histamine. Finally acid secretion of stimulated fundic glands could not be inhibited by the H$^+$, K$^+$-ATPase inhibitor omeprazole.

CONCLUSION

The fundic region of the stomach secreted acid via the H$^+$,K$^+$ ATPase, and was not sensitive to proton pump inhibitors. Our findings demonstrate that the fundic region of the stomach is much more than a holding area and in fact can secrete acid in response to secretagogue stimulation, except histamine.

The digestion of food by the stomach requires a complex combination of hormonal and neuronal events. Generally it has been thought that the corpus or body of the stomach secretes acid via the parietal cells and the antrum secretes bicarbonate to neutralize the digestate by raising the pH of the stomach contents [1a-9a]. During this process the peristaltic movements of the stomach result in contractions that push the food upward into the fundic section of the stomach where it transits before exiting into the small intestine[10a]. In this model of digestion the fundus acts only as a holding zone and is not involved in acid secretion[4a-11a]. Classical gastric acid secretion in the corpus occurs when the H$^+$, K$^+$-ATPase gets stimulated by secretagogues and begins to secrete protons into the secretory canaliculus after being trafficked to the apical membrane from their cytoplasmic tubulovesicles[12a]. The parietal cell has at least three activating receptors on its basolateral membrane, i.e. histamine H2, acetylcholine M3 and Gastrin CCK-B. It is well accepted that the H2 receptor couples to Gs to activated adenylate cyclase producing cAMP and subsequent activation of cAMP dependant protein kinase. The acetylcholine and gastrin receptor couple through a non Gs system probably Gq to activate phospholipase C producing IP3 and diacylglycerol. Acetylcholine releases intracellular Ca$^{2+}$ and gastrin activating protein kinase C[13a]. After this cascade of intracellular events the parietal cell extrudes protons via the H$^+$, K$^+$-ATPase pump which exchanges intracellular H$^+$ ions for extracellular K$^+$ ions in an electroneutral ratio[14a].

Recent observations in patients who have undergone gastric bypass surgery present an interesting paradigm, namely that only left with a small fundic region postoperatively, they still have acid secretion which in some patients leads to reflux symptoms, ulcers and enteric content leaks[15a]. Of note is that many of these patients have little success in abating the symptoms while on proton pump inhibitor (PPI) therapy[16a-18a].

From these initial clinical observations we raised the question: does the fundus play a role in the production of acid, and how similar are its properties to corpus secretory proteins. We also were interested in determining fundic sensitivity to classical secretagogues and therefore conducted studies using histamine, pentagastrin, and acetylcholine.

In the present experiment we have investigated the acid secretory properties of the rat fundus under resting and secretagogue stimulated states, furthermore we elucidate fundic response to an inhibitory drug of acid secretion. Our data demonstrate that the fundic region is an active secretory zone in the stomach and contains a gastric $H^+$, $K^+$-ATPase that can be stimulated by secretagogues but appears to be insensitive to omeprazole. Zinc therapy according to the present invention is a means to regulate acid release in the fundus region.

REFERENCES

First Set

1. Hersey S J, Sachs G. Gastric acid secretion. *Physiol Rev* 1995; 75:155-189.
2. Sachs G, Prinz C, Loo D, Bamberg K, Besancon M, Shin J M. Gastric acid secretion: activation and inhibition. *Yale J Biol Med* 1994; 67:81-95.
3. Sachs G. Physiology of the parietal cell and therapeutic implications. *Pharmacotherapy* 2003; 23:68 S-73S.
4. Horie S, Yano S, Watanabe K. Effects of drugs acting on Cl(−)-. *Eur J Pharmacol* 1992; 229:15-19.
5. Helander H F, Keeling D J. Cell biology of gastric acid secretion. Baillieres Clin Gastroenterol 1993; 7:1-21.
6. Soumarmon A, Lewin M J. Gastric (H+,K+)-ATPase. Biochimie 1986; 68:1287-1291.
7. Wolfe M M, Welage L S, Sachs G. Proton pump inhibitors and gastric acid secretion. Am J Gastroenterol 2001; 96:3467-3468.
8. Aihara T, Nakamura E, Amagase K, Tomita K, Fujishita T, Furutani K, Okabe S. Pharmacological control of gastric acid secretion for the treatment of acid-related peptic disease: past, present, and future. Pharmacol Ther 2003; 98:109-127.
9. Gardner J D, Sloan S, Miner P B, Robinson M. Meal-stimulated gastric acid secretion and integrated gastric acidity in gastro-oesophageal reflux disease. Aliment Pharmacol Ther 2003; 17:945-953.
10. Williams J L. Gastroesophageal reflux disease: clinical manifestations. Gastroenterol Nurs 2003; 26:195-200.
11. Lehmann F, Hildebrand P, Beglinger C. New molecular targets for treatment of peptic ulcer disease. Drugs 2003; 63:1785-1797.
12. Brzozowski T, Konturek P C, Konturek S J, Drozdowicz D, Kwiecien S, Pajdo R, Bielanski W, Hahn E G. Role of gastric acid secretion in progression of acute gastric erosions induced by ischemia-reperfusion into gastric ulcers. Eur J Pharmacol 2000; 398:147-158.
13. Franzin G, Manfrini C, Musola R, Rodella S, Fratton A. Chronic erosions of the stomach—a clinical, endoscopic and histological evaluation. Endoscopy 1984; 16:1-5.
14. Raugstad T S, Svanes K, Ulven A, Moister A. Interaction between acute gastric ulcer and epinephrine-induced mucosal erosions in the rat: the significance of gastric acid secretion. Digestion 1979; 19:70-72.
15. Houghton J, Stoicov C, Nomura S, Rogers A B, Carlson J, Li H, Cai X, Fox J G, Goldenring J R, Wang T C. Gastric cancer originating from bone marrow-derived cells. Science 2004; 306:1568-1571.
16. Bell N J, Hunt R H. Progress with proton pump inhibition. Yale J Biol Med 1992; 65:649-657.
17. Garnett W R. Lansoprazole: a proton pump inhibitor. Ann Pharmacother 1996; 30:1425-1436.
18. Robinson M. Drugs, bugs, and esophageal pH profiles. Yale J Biol Med 1999; 72:169-172.
19. Tutuian R, Katz P O, Castell D O. Nocturnal acid breakthrough: pH, drugs and bugs. Eur J Gastroenterol Hepatol 2004; 16:441-443.
20. Adachi K, Komazawa Y, Fujishiro H, Mihara T, Ono M, Yuki M, Kawamura A, Karim Rumi M A, Amano Y, Kinoshita Y. Nocturnal gastric acid breakthrough during the administration of rabeprazole and ranitidine in *Helicobacter pylori*-negative subjects: effects of different regimens. J Gastroenterol 2003; 38:830-835.
21. Kleinman L, McIntosh E, Ryan M, Schmier J, Crawley J, Locke G R, III, De L G. Willingness to pay for complete symptom relief of gastroesophageal reflux disease. Arch Intern Med 2002; 162:1361-1366.
22. Carlsson R, Galmiche J P, Dent J, Lundell L, Frison L. Prognostic factors influencing relapse of oesophagitis during maintenance therapy with antisecretory drugs: a meta-analysis of long-term omeprazole trials. Aliment Pharmacol Ther 1997; 11:473-482.
23. Katz P O, Hatlebakk J G, Castell D O. Gastric acidity and acid breakthrough with twice-daily omeprazole or lansoprazole. Aliment Pharmacol Ther 2000; 14:709-714.
24. Tytgat G N. Shortcomings of the first-generation proton pump inhibitors. Eur J Gastroenterol Hepatol 2001; 13 Suppl 1: S29-S33.
25. Gedda K, Scott D, Besancon M, Lorentzon P, Sachs G. Turnover of the gastric H+,K(+)-adenosine triphosphatase alpha subunit and its effect on inhibition of rat gastric acid secretion. Gastroenterology 1995; 109:1134-1141.
26. Diamond I, Hurley L S. Histopathology of zinc-deficient fetal rats. J Nutr 1970; 100:325-329.
27. Elmes M E, Jones J G. Ultrastructural studies on Paneth cell apoptosis in zinc deficient rats. Cell Tissue Res 1980; 208:57-63.
28. Fong L Y, Lee J S, Chan W C, Newberne P M. Zinc deficiency and the development of esophageal and forestomach tumors in Sprague-Dawley rats fed precursors of N-nitroso-N-benzylmethylamine. J Natl Cancer Inst 1984; 72:419-425.
29. Ng W L, Fong L Y, Ma L, Newberne P M. Dietary zinc deficiency and tumorigenesis: a scanning electron microscope study. J Electron Microsc (Tokyo) 1984; 33:344-348.
30. Sunderman F W, Jr. The influence of zinc on apoptosis. Ann Clin Lab Sci 1995; 25:134-142.
31. Cho C H, Fong L Y, Ma P C, Ogle C W. Zinc deficiency: its role in gastric secretion and stress-induced gastric ulceration in rats. Pharmacol Biochem Behav 1987; 26:293-297.
32. Cho C H, Fong L Y, Wong S H, Ogle C W. Zinc deficiency worsens ethanol-induced gastric ulcers in rats. Drug Nutr Interact 1988; 5:289-295.
33. Frommer D J. The healing of gastric ulcers by zinc sulphate. Med J Aust 1975; 2:793-796.
34. Watanabe T, Arakawa T, Fukuda T, Higuchi K, Kobayashi K. Zinc deficiency delays gastric ulcer healing in rats. Dig Dis Sci 1995; 40:1340-1344.
35. Naess K. [Zinc in the treatment of stomach ulcer]. Tidsskr Nor Laegeforen 1976; 96:1334.
36. Kirchhoff P, Wagner C A, Gaetzschmann F, Radebold K, Geibel J P. Demonstration of a functional apical sodium 37. McDaniel N, Lytle C. Parietal cells express high levels of Na—K-2Cl cotransporter on migrating into the gastric gland neck. Am J Physiol 1999; 276:G1273-G1278.
38. Geibel J P, Wagner C A, Caroppo R, Qureshi I, Gloeckner J, Manuelidis L, Kirchhoff P, Radebold K. The stomach divalent ion-sensing receptor scar is a modulator of gastric acid secretion. J Biol Chem 2001; 276:39549-39552.
39. Dufner M M, Kirchhoff P, Remy C, Hafner P, Muller M K, Cheng S X, Tang L Q, Hebert S C, Geibel J P, Wagner C A. The Calcium-Sensing Receptor (CaSR) acts as a modulator of gastric acid secretion in freshly isolated human gastric glands. Am J Physiol Gastrointest Liver Physiol 2005.
40. Schultheis P J, Clarke L L, Meneton P, Harline M, Boivin G P, Stemmermann G, Duffy J J, Doetschman T, Miller M L, Shull G E. Targeted disruption of the murine Na+/H+ exchanger isoform 2 gene causes reduced viability of gastric parietal cells and loss of net acid secretion. J Clin Invest 1998; 101:1243-1253.
41. Kirchhoff P, Andersson K, Socrates T, Sidani S M, Kosiek O, Geibel J P. Characteristics of the K+-competitive H+,K+-ATPase Inhibitor AZD0865 in isolated rat gastric glands. Am J Physiol Gastrointest Liver Physiol 2006.
42. Andersson K, Carlsson E. Potassium-competitive acid blockade: a new therapeutic strategy in acid-related diseases. Pharmacol Ther 2005; 108:294-307.
43. Dammann H G, Burkhardt F. Pantoprazole versus omeprazole: influence on meal-stimulated gastric acid secretion. Eur J Gastroenterol Hepatol 1999; 11:1277-1282.

Second Set References

1a. Sachs G. The parietal cell as a therapeutic target. Scand J Gastroenterol Suppl 1986; 118:1-10.
2a. Lorentzon P, Scott D, Hersey S, Wallmark B, Rabon E, Sachs G. The gastric H+,K+-ATPase. Prog Clin Biol Res 1988; 273:247-254.
3a. Wallmark B, Lorentzon P, Sachs G. The gastric H+,K(+)-ATPase. J Intern Med Suppl 1990; 732:3-8.
4a. Prinz C, Kajimura M, Scott D, Helander H, Shin J, Besancon M, Bamberg K, Hersey S, Sachs G. Acid secretion and the H,K ATPase of stomach. Yale J Biol Med 1992; 65:577-596.
5a. Scott D R, Helander H F, Hersey S J, Sachs G. The site of acid secretion in the mammalian parietal cell. Biochim Biophys Acta 1993; 1146:73-80.
6a. Sachs G, Prinz C, Loo D, Bamberg K, Besancon M, Shin J M. Gastric acid secretion: activation and inhibition. Yale J Biol Med 1994; 67:81-95.
7a. Hersey S J, Sachs G. Gastric-Acid Secretion. Physiological Reviews 1995; 75:155-189.
8a. Hirschowitz B I, Keeling D, Lewin M, Okabe S, Parsons M, Sewing K, Wallmark B, Sachs G. Pharmacological Aspects of Acid-Secretion. Digestive Diseases and Sciences 1995; 40:S3-S23.
9a. Wolfe M M, Welage L S, Sachs G. Proton pump inhibitors and gastric acid secretion. Am J Gastroenterol 2001; 96:3467-3468.
10a. Hersey S J, Sachs G. Gastric-Acid Secretion. Physiological Reviews 1995; 75:155-189.
11a. Hersey S J, Sachs G. Gastric-Acid Secretion. Physiological Reviews 1995; 75:155-189.
12a. Forte J G, Ly B, Rong Q, Ogihara S, Ramilo M, Agnew B, Yao X. State of actin in gastric parietal cells. Am J Physiol 1998; 274:C97-104.
13a. Urushidani T, Forte J G. Signal transduction and activation of acid secretion in the parietal cell. J Membr Biol 1997; 159:99-111.
14a. Geibel J P. Role of potassium in acid secretion. World J Gastroenterol 2005; 11:5259-5265.
15a. Blachar A, Federle M P. Gastrointestinal complications of laparoscopic roux-en-Y gastric bypass surgery in patients who are morbidly obese: findings on radiography and CT. AJR Am J Roentgenol 2002; 179:1437-1442.
16a. Peghini P L, Katz P O, Castell D O. Ranitidine controls nocturnal gastric acid breakthrough on omeprazole: a controlled study in normal subjects. Gastroenterology 1998; 115:1335-1339.
17a. Peghini P L, Katz P O, Bracy N A, Castell D O. Nocturnal recovery of gastric acid secretion with twice-daily dosing of proton pump inhibitors. Am J Gastroenterol 1998; 93:763-767.
18a. Sanders S W, Moore J G, Day G M, Tolman K G. Circadian differences in pharmacological blockade of meal-stimulated gastric acid secretion. Aliment Pharmacol Ther 1992; 6:187-193.
19a. Knauf F, Yang C L, Thomson R B, Mentone S A, Giebisch G, Aronson P S. Identification of a chloride-formate exchanger expressed on the brush border membrane of renal proximal tubule cells. Proc Natl Acad Sci USA 2001; 98:9425-9430.
20a. Dufner M M, Kirchhoff P, Remy C, Hafner P, Muller M K, Cheng S X, Tang L Q, Hebert S C, Geibel J P, Wagner C A. The calcium-sensing receptor acts as a modulator of gastric acid secretion in freshly isolated human gastric glands. Am J Physiol Gastrointest Liver Physiol 2005; 289:G1084-G1090.
21a. Kirchhoff P, Dave M H, Remy C, Kosiek O, Busque S M, Dufner M, Geibel J P, Verrey F, Wagner C A. An amino acid transporter involved in gastric acid secretion. Pflugers Arch 2006; 451:738-748.
22a. Waisbren S J, Geibel J, Boron W F, Modlin I M. Luminal perfusion of isolated gastric glands. Am J Physiol 1994; 266:C1013-C1027.
23a. Waisbren S J, Geibel J P, Modlin I M, Boron W F. Unusual permeability properties of gastric gland cells. Nature 1994; 368:332-335.
24a. Busque S M, Kerstetter J E, Geibel J P, Insogna K. L-type amino acids stimulate gastric acid secretion by activation of the calcium-sensing receptor in parietal cells. Am J Physiol Gastrointest Liver Physiol 2005; 289:G664-G669.
25a. Geibel J P, Wagner C A, Caroppo R, Qureshi I, Gloeckner J, Manuelidis L, Kirchhoff P, Radebold K. The stomach divalent ion-sensing receptor scar is a modulator of gastric acid secretion. J Biol Chem 2001; 276:39549-39552.
26a. Sachs G, Scott D, Reuben M. Omeprazole and the gastric mucosa. Digestion 1990; 47 Suppl 1:35-38.
27a. Sachs G, Wallmark B. The gastric H+,K+-ATPase: the site of action of omeprazole. Scand J Gastroenterol Suppl 1989; 166:3-11.
28a. Alino S F, Garcia D, Uvnas-Moberg K. On the interaction between intragastric pH and electrical vagal stimulation in causing gastric acid secretion and intraluminal release of gastrin and somatostatin in anesthetized rats. Acta Physiol Scand 1983; 117:491-495.
29a. Meulemans A L, Eelen J G, Schuurkes J A. NO mediates gastric relaxation after brief vagal stimulation in anesthetized dogs. Am J Physiol 1995; 269:G255-G261.
30a. Singh J. Prostaglandin release from rat stomach following vagal stimulation or administration of acetylcholine. Eur J Pharmacol 1980; 65:39-48.

31a. Aarimaa M, Soderstrom K O, Kalimo H, Inberg M, Nevalainen T. Morphology and function of the parietal cells after proximal selective vagotomy in duodenal ulcer patients. Scand J Gastroenterol 1984; 19:787-797.

32a. Amdrup E. The surgical treatment of duodenal ulcer. Schweiz Med Wochenschr 1979; 109:583-585.

33a. Waisbren S J, Modlin I M. The evolution of therapeutic vagotomy. Surg Gynecol Obstet 1990; 170:261-272.

34a. Abelo A, Eriksson U G, Karlsson M O, Larsson H, Gabrielsson J. A turnover model of irreversible inhibition of gastric acid secretion by omeprazole in the dog. J Pharmacol Exp Ther 2000; 295:662-669.

35a. Andersen J B, Andrade D V, Wang T. Effects of inhibition gastric acid secretion on arterial acid-base status during digestion in the toad *Bufo marinus*. Comp Biochem Physiol A Mol Integr Physiol 2003; 135:425-433.

36a. Gedda K, Scott D, Besancon M, Lorentzon P, Sachs G. Turnover of the gastric H+,K(+)-adenosine triphosphatase alpha subunit and its effect on inhibition of rat gastric acid secretion. Gastroenterology 1995; 109:1134-1141.

37a. Sachs G, Shin J M, Pratha V, Hogan D. Synthesis or rupture: duration of acid inhibition by proton pump inhibitors. Drugs Today (Barc) 2003; 39 Suppl A:11-14.

38a. Shamburek R D, Schubert M L. Pharmacology of gastric acid inhibition. Baillieres Clin Gastroenterol 1993; 7:23-54.

39a. Locke G R, III. Current medical management of gastroesophageal reflux disease. Thorac Surg Clin 2005; 15:369-375.

40a. Geibel J P. Secretion and absorption by colonic crypts. Annu Rev Physiol 2005; 67:471-490.

The invention claimed is:

1. A pharmaceutical composition in oral dosage form for oral administration to a human patient in need consisting essentially of effective amounts of at least one pharmaceutically acceptable water soluble zinc salt in an amount which rapidly elevates the pH of gastric juices of a patient after oral administration to a pH of at least about 3.0 within no more than about one hour after said composition is orally administered to said patient in combination with an anticancer effective amount of at least one chemotherapeutic agent in said composition which is degraded by acid in the stomach of said patient such that said therapeutic agent(s) exhibits greater bioavailability when administered in combination with said water soluble zinc salt than in the absence of said water soluble zinc salt due to the increase in the pH of the gastric juices effected by said zinc salt, optionally in combination with a pharmaceutically acceptable carrier, additive or excipient, wherein said water soluble zinc salt is selected from the group consisting of zinc chloride, zinc gluconate, zinc acetate or a mixture thereof.

2. The composition according to claim 1 wherein said water soluble zinc salt is zinc acetate.

3. The composition according to claim 1 wherein said mixture of water soluble zinc salts comprises two water soluble zinc salts.

4. The composition according to claim 1 wherein said zinc salt is zinc chloride.

5. The composition according to claim 3 wherein said water soluble zinc salt is zinc gluconate.

6. The composition according to claim 3 wherein said two water soluble zinc salts are zinc chloride and zinc gluconate.

7. The composition according to claim 1 wherein said chemotherapeutic agent is selected from the group consisting of 13-cis-Retinoic Acid; 2-Chlorodeoxyadenosine; 5-Azacitidine; 5-Fluorouracil; 6-Mercaptopurine; 6-Thioguanine; Abraxane; Isotretinoin; Actinomycin-D; Doxorubicin Hydrochloride; Anagrelide; Hydrocortisone; Aldesleukin; Alemtuzumab; Pemetrexed; Alitretinoin; Vinblastine; Melphalan; All-transretinoic Acid; Alphahlterferon; Altretamine; Amethopterin; Amifostine; Aminoglutethimide; Aminoglutethimide; Anagrelide; Asparaginase; Hydrocortone Phosphate; Leurocristine; Lenalidomide; Letrozole; Leucovorin; Leukeran; Sargramostim; Leuprolide; Cladribin; Liposomal Ara-C; Deltasone; Lomustine; L-phenylalanine mustard; L-Sarcolysin; Leuprolide Acetate; Procarbazine; Maxidex; Mechlorethamine; Mechlorethamine Hydrochloride; Methylprednisolone; Megestrol Acetate; Melphalan; Mercaptopurine; Mesna; Methotrexate; Nilutamide; Anastrozole; Arabinosylcytosine; Darbepoetin Alpha; Pamidronate; Exemestane; Nelarabine; Arsenic Trioxide; Atragen; Bevacizumab; Azacitidine; BCG (Bacillus Calmette Guerin); BCNU (Carmustine); Bexarotene; Tositumomab; Bicalutamide; Bleomycin; Bortezomib; Busulfan; Eribitux; Calcium Leucovorin; Alemtuzumab; Irinotecan hydrochloride; Camptothecin-11; Capecitabine; Carboplatin; Bicalutamide; CC-5013 (Revlimid); CCNU (lomustine); CDDP (Cisplatin); CeeNU; Daunorubicin; Cetuximab; Chlorambucil; Mitomycin; Mitomycin-C; Mitoxantrone; Mustine; Mitomycin; Hydroxyurea; Gemtuzumab Ozogamicin; Vinorelbine Tartrate; Nelarabine; Cyclophosphamide; Pegfilgrastim; Oprelvekin; Filgrastim; Sorafenib; Nilutamide; Pentostatin; Nitrogen Mustard; Genox; Mitoxantrone; Octreotide; Octreotide acetate; Pegylated asparaginase; Denileukin Diftitox; Paclitaxel; Oprevelkin; Prednisolone Sodium Phosphate; Prednisone; Oxaliplatin; Paclitaxel Protein-bound; Pamidronate; Panitumumab; Paraplatin; Dactinomycin; Topotecan; Cyclophosphamide; Aminoglutethimide; Cytarabine; Cytarabine Liposomal; Dacarbazine; Dacogen; Dactinomycin; Dasatinib; Daunomycin; Daunorubicin Hydrochloride; Daunorubicin Liposomal; Decadron; Decitabine; Prednisolone; Prednisone; Denileukin diftitox; Dexamethasone; Dexamethasone acetate; Dexamethasone Sodium Phosphate; Dexasone; Dexrazoxane; Novantrone; Diodex; Docetaxel; Doxorubicin; Hydroxyurea; Dacarbazine; PEG Interferon; Pegaspargase; Pegfilgrastim; Peginterferon alfa-2b; PEG-L-asparaginase; PEMETREXED; Pentostatin; Phenylalanine Mustard; Procarbazine; Epoetin Alfa; Aldesleukin; Prolifeprospan 20 with Carmustine; Mercaptopurine; Raloxifene; Trexall; Rituximab; Rubidomycin hydrochloride; Octreotide Acetate; Hydrocortisone Sodium Succinate; Methylprednisolone sodium succinate; Sorafenib; Dasatinib; Gleevec; Streptozocin; SU11248; Sunitinib; Sunitinib Malate; Tamoxifen; Erlotinib; Bexarotene; Epirubicin hydrochloride; Oxaliplatin; Estramustine; Epirubicin; Epoetin alfa; Cetuximab; Erlotinib; Erwinia L-asparaginase; Ethyol; Etoposide Phosphate; Etoposide; Flutamide; Raloxifene; Exemestane; Toremifene; Fulvestrant; Letrozole; Filgrastim; Floxuridine; Fludarabine; Fluoxymesterone; Flutamide; Floxuridine; Fulvestrant; Neupogen; Gefitinib; Gemcitabine; Gemtuzumab; ozogamicin; Carmustine Wafer; Goserelin; Granulocyte Colony Stimulating Factor; Docetaxel; Temozolonaide; Teniposide; Thiotepa; Thalidomide; BCG (TheraCys strain); Thioguanine; Thiophosphamide; Thiotepa; Etoposide; Topotecan; Toremifene; Tositumomab; Trastuzumab; Tretinoin; Arsenic; VCR; Panitumumab; Vinblastine Sulfate Bortezomib; Azacitidine; Vinblastine; Vinblastine Sulfate; Vincristine; Vinorelbine; Vinorelbine tartrate; VM-26; Vorinostat; Teniposide; Capecitabine); Streptozocin; Fluoxymesterone; Trastuzumab; Hexadrol; Altretamin; Hexamethylmelamine; Hycamtin; Hydroxyurea; Ibritumomab; Ibritumornab Tiuxetan; Idarubicin; Ifosfamide; IFN-alpha; IL-11; IL-2; Imatinib mesylate; Imidazole Carboxamide; Interferon alfa; Interferon Alfa-2b (PEG Conjugate); Interleukin-2; interleukin-11; interferon alfa-2b; Getfitinib; Irinotecan; Isotretinoin; Dexrazoxane; Goserelin; Zoledronic acid; Zolinza and mixtures thereof.

8. The composition according to claim 1 wherein said therapeutic agent is a mixture of chemotherapeutic agent(s).

9. A method of increasing the bioavailability and/or reducing or alleviating the side effects of at least one orally administered chemotherapeutic agent in the treatment of cancer in a human patient which is unstable to low pH in the stomach of said patient after oral administration comprising administering a composition consisting essentially of an anticancer effective amount of said agent(s) in combination with an effective amount of at least one pharmaceutically acceptable water soluble zinc salt which rapidly raises the pH of gastric juice in the stomach of said patient to at least about 3.0 after no longer than about one hour after oral administration to said patient such that said chemotherapeutic agent(s) exhibits greater bioavailability and/or reduced side effects when administered in combination with said water soluble zinc salt than in the absence of said water soluble zinc salt due to the increase in the pH of the gastric juices effected by said water soluble zinc salt, wherein said water soluble zinc salt is selected from the group consisting of zinc chloride, zinc gluconate, zinc acetate or a mixture thereof.

10. The method according to claim 9 wherein said water soluble zinc salt is zinc acetate.

11. The method according to claim 9 wherein said mixture of water soluble zinc salts comprises two water soluble zinc salts.

12. The method according to claim 9 wherein said water soluble zinc salt is zinc chloride.

13. The method according to claim 9 wherein said water soluble zinc salt is zinc gluconate.

14. The method according to claim 11 wherein said two water soluble zinc salts are zinc chloride and zinc gluconate.

15. The method according to any of claims 9-14 wherein said chemotherapeutic agent(s) is selected from the group consisting of selected from the group consisting of 13-cis-Retinoic Acid; 2-Chlorodeoxyadenosine; 5-Azacitidine; 5-Fluorouracil; 6-Mercaptopurine; 6-Thioguanine; Abraxane; Isotretinoin; Actinomycin-D; Doxorubicin Hydrochloride; Anagrelide; Hydrocortisone; Aldesleukin; Alemtuzumab; Pemetrexed; Alitretinoin; Vinblastine; Melphalan; All-transretinoic Acid; Alphahlterferon; Altretamine; Amethopterin; Amifostine; Aminoglutethimide; Aminoglutethimide; Anagrelide; Asparaginase; Hydrocortone Phosphate; Leurocristine; Lenalidomide; Letrozole; Leucovorin; Leukeran; Sargramostim; Leuprolide; Cladribin; Liposomal Ara-C; Deltasone; Lomustine; L-phenylalanine mustard; L-Sarcolysin; Leuprolide Acetate; Procarbazine; Maxidex; Mechlorethamine; Mechlorethamine Hydrochloride; Methylprednisolone; Megestrol Acetate; Melphalan; Mercaptopurine; Mesna; Methotrexate; Nilutamide; Anastrozole; Arabinosylcytosine; Darbepoetin Alpha; Pamidronate; Exemestane); Nelarabine; Arsenic Trioxide; Atragen; Bevacizumab; Azacitidine; BCG (Bacillus Calmette Guerin); BCNU (Carmustine); Bexarotene; Tositumomab; Bicalutamide; Bleomycin; Bortezomib; Busulfan; Eribitux; Calcium Leucovorin; Alemtuzumab; Irinotecan hydrochloride; Camptothecin-11; Capecitabine; Carboplatin; Bicalutamide; CC-5013 (Revlimid); CCNU (lomustine); CDDP (Cisplatin); CeeNU; Daunorubicin; Cetuximab; Chlorambucil; Mitomycin; Mitomycin-C; Mitoxantrone; Mustine; Mitomycin; Hydroxyurea; Gemtuzumab Ozogamicin; Vinorelbine Tartrate; Nelarabine; Cyclophosphamide; Pegfilgrastim; Oprelvekin; Filgrastim; Sorafenib; Nilutamide); Pentostatin; Nitrogen Mustard; Genox; Mitoxantrone; Octreotide; Octreotide acetate; Pegylated asparaginase; Denileukin Diftitox; Paclitaxel; Oprevelkin; Prednisolone Sodium Phosphate; Prednisone; Oxaliplatin; Paclitaxel Protein-bound; Pamidronate; Panitumumab; Paraplatin; Dactinomycin; Topotecan; Cyclophosphamide; Aminoglutethimide; Cytarabine; Cytarabine Liposomal; Dacarbazine; Dacogen; Dactinomycin; Dasatinib; Daunomycin; Daunorubicin Hydrochloride; Daunorubicin Liposomal; Decadron; Decitabine; Prednisolone; Prednisone; Denileukin diftitox; Dexamethasone; Dexamethasone acetate; Dexamethasone Sodium Phosphate; Dexasone; Dexrazoxane; Novantrone; Diodex; Docetaxel; Doxorubicin; Hydroxyurea; Dacarbazine; PEG Interferon; Pegaspargase; Pegfilgrastim; Peginterferon alfa-2b; PEG-L-asparaginase; PEMETREXED; Pentostatin; Phenylalanine Mustard; Procarbazine; Epoetin Alfa; Aldesleukin; Prolifeprospan 20 with Carmustine; Mercaptopurine; Raloxifene; Trexall; Rituximab; adriamycin; Rubidomycin hydrochloride; Octreotide Acetate; Hydrocortisone Sodium Succinate; Methylprednisolone sodium succinate; Sorafenib; Dasatinib; Gleevec; Streptozocin; SU11248; Sunitinib; Sunitinib Malate; Tamoxifen; Erlotinib; Bexarotene; Epirubicin hydrochloride; Oxaliplatin; Estramustine; Epirubicin; Epoetin alfa; Cetuximab; Erlotinib; Erwinia L-asparaginase; Ethyol; Etoposide Phosphate; Etoposide; Flutamide; Raloxifene; Exemestane; Toremifene; Fulvestrant; Letrozole; Filgrastim; Floxuridine; Fludarabine; Fluoxymesterone; Flutamide; Floxuridine; Fulvestrant; Neupogen; Gefitinib; Gemcitabine; Gemtuzumab; ozogamicin; Carmustine Wafer; Goserelin; Granulocyte Colony Stimulating Factor; Docetaxel; Temozolomide; Teniposide; Thiotepa; Thalidomide; BCG (TheraCys strain); Thioguanine; Thiophosphamide; Thiotepa; Etoposide; Topotecan; Toremifene; Tositumomab; Trastuzumab; Tretinoin; Arsenic; VCR; Panitumumab; Vinblastine Sulfate Bortezomib; Azacitidine; Vinblastine; Vinblastine Sulfate; Vincristine; Vinorelbine; Vinorelbine tartrate; VM-26; Vorinostat; Teniposide; Capecitabine); Streptozocin; Fluoxymesterone; Trastuzumab; Hexadrol; Altretamin; Hexamethylmelamine; Hycamtin; Hydroxyurea; Ibritumomab; Ibritumomab Tiuxetan; Idarubicin; Ifosfamide; MN-alpha; IL-11; IL-2; Imatinib mesylate; Imidazole Carboxamide; Interferon alfa; Interferon Alfa-2b (PEG Conjugate); Interleukin-2; Interleukin-11; interferon alfa-2b; Getfitinib; Irinotecan; Isotretinoin; Dexrazoxane; Goserelin; Zoledronic acid; Zolinza and mixtures thereof.

16. The method according to claim 9 wherein said chemotherapeutic agent(s) is a mixture of chemotherapeutic agents.

17. The composition according to claim 3 wherein said two water soluble zinc salts are zinc acetate and zinc chloride.

18. The composition according to claim 3 wherein said two water soluble zinc salts are zinc acetate and zinc gluconate.

19. The method according to claim 11 wherein said two water soluble zinc salts are zinc acetate and zinc chloride.

20. The composition according to claim 11 wherein said two water soluble zinc salts are zinc acetate and zinc gluconate.

* * * * *